US012213989B2

(12) United States Patent
Song et al.

(10) Patent No.: US 12,213,989 B2
(45) Date of Patent: Feb. 4, 2025

(54) USE OF MARIBAVIR IN TREATMENT REGIMENS

(71) Applicant: Takeda Pharmaceutical Company Limited, Osaka (JP)

(72) Inventors: Heng Song, Lexington, MA (US); Kefeng Sun, Needham, MA (US); Matthew Crouthamel, Chelmsford, MA (US); Grace Chen, Libertyville, IL (US); Andy Z. X. Zhu, Winchester, MA (US); Ingrid Nicolle Michon, Voorschoten (NL); Howard James Burt, Sheffield (GB); Zoe Elizabeth Barter, Nottingham (GB); Sibylle Neuhoff, Sheffield (GB)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 18/646,035

(22) Filed: Apr. 25, 2024

(65) Prior Publication Data

US 2024/0285663 A1 Aug. 29, 2024

Related U.S. Application Data

(63) Continuation of application No. 18/400,304, filed on Dec. 29, 2023, now abandoned, which is a continuation of application No. PCT/US2022/050341, filed on Nov. 18, 2022.

(60) Provisional application No. 63/281,206, filed on Nov. 19, 2021.

(51) Int. Cl.
*A61K 31/7056* (2006.01)
*A61K 31/4166* (2006.01)
*A61K 31/513* (2006.01)
*A61K 31/55* (2006.01)

(52) U.S. Cl.
CPC ...... *A61K 31/7056* (2013.01); *A61K 31/4166* (2013.01); *A61K 31/513* (2013.01); *A61K 31/55* (2013.01)

(58) Field of Classification Search
CPC ............ A61K 31/7056; A61K 31/4166; A61K 31/513; A61K 31/55
USPC ........................................................ 514/43
See application file for complete search history.

(56) References Cited

FOREIGN PATENT DOCUMENTS

| WO | 2019180708 A1 | 9/2019 |
|---|---|---|
| WO | 2023091625 A1 | 5/2023 |

OTHER PUBLICATIONS

Glossary of medical education terms, Institute of International Medical Education. http://www.iime.org/glossary.htm Accessed in Mar. 2013. (Year: 2013).*
Piret et al. Clinical development of letermovir and maribavir: Overview of human cytomegalovirus drug resistance. Antiviral Research 163 (2019) 91-105. (Year: 2019).*
Alain et al. Maribavir Use in Practice for Cytomegalovirus Infection in French Transplantation Centers. Transplantation Proceedings, 45, 1603-1607 (2013). (Year: 2013).*
Asconape JJ. Pharmacokinetic Considerations with the Use of Antiepileptic Drugs in Patients with HIV and Organ Transplants. Current Neurology and Neuroscience Reports (2018) 18: 89, pp. 1-8. (Year: 2018).*
International Search Report for PCT/US2022/050341, filed Nov. 18, 2022, 4 pages, (mailed Mar. 15, 2023).
Marbury, T., Poster Session III (PIII 1-88), Clinical Pharmacology and Therapeutics, 85(16):S68-S96 (2009).
Pescovitz, M.D. et al., A randomized, double-blind, pharmacokinetic study of oral maribavir with tacrolimus in stable renal transplant recipients, Am. J. Transplant., 9(10):2324-2330 (2009).
Song, I. et al., Clinical Pharmacology of Maribavir (SHP620): A Comprehensive Overview, Abstract No. 510, Biology of Blood and Marrow Transplantation, 25(3):1 page, (2019).
Song, I. et al., Summary of Maribavir (SHP620) Drug-Drug Interactions Based on Accumulated Clinical and Nonclinical Data, Abstract No. 556, Biology of Blood and Marrow Transplantation, 25(3):2 pages, (2019).
Song, I.H. et al., Effects of Maribavir on P-Glycoprotein and CYP2D6 in Healthy Volunteers, J. Clin. Pharmacol., 60(1):96-106 (2020).
Stern, A. and Papanicolaou, G.A., CMV Prevention and Treatment in Transplantation: What's New in 2019, Curr. Infect. Dis. Rep., 21(11):45 (2019).
Written Opinion for PCT/US2022/050341, filed Nov. 18, 2022, 6 pages, (mailed Mar. 15, 2023).
Medsafe, "Drug Metabolism—The Importance of Cytochrome P450 3A4", Prescriber Update 35(1):4-6, [retrieved from the Internet on Aug. 30, 2024] <URL: https://www.medsafe.govt.nz/profs/PUArticles/March2014DrugMetabolismCytochromeP4503A4.htm>, Published Mar. 6, 2014

* cited by examiner

*Primary Examiner* — Yih-Horng Shiao
(74) *Attorney, Agent, or Firm* — Honigman LLP; Andrew S. Chipouras; Jonathan P. O'Brien

(57) ABSTRACT

Characterization of drug-drug interaction properties and pharmacological properties of maribavir is useful to inform potential drug-drug interactions and dosing strategies when administering with co-medications.

7 Claims, 4 Drawing Sheets

USE OF MARIBAVIR IN TREATMENT REGIMENS

CROSS REFERENCE TO RELATED APPLICATION

The present application is a continuation application of U.S. application Ser. No. 18/400,304, filed Dec. 29, 2023, which is a continuation application of PCT Application No. PCT/US22/50341, filed Nov. 11, 2022, which claims priority to U.S. Provisional Application No. 63/281,206, filed Nov. 19, 2021, each of which is incorporated herein by reference in its entirety.

BACKGROUND

Cytomegalovirus (CMV) infection and disease are significant post-transplant complications and are associated with substantial morbidity and reduced long-term survival among transplant recipients. There are currently no approved therapies for the treatment of CMV infection in transplant recipients.

Transplant patients often receive numerous concomitant medications to manage their comorbidities. Characterization of drug-drug interaction properties and pharmacological properties of maribavir is useful to inform potential drug-drug interactions and dosing strategies when administering with co-medications.

SUMMARY

Maribavir is a benzimidazole riboside, and is an orally available antiviral medication against cytomegalovirus (CMV). Maribavir is also known under its trade name LIVTENCITY™. Typically, patients (e.g., adults and/or children over 12 years of age and weighing at least 35 kg) are administered 400 mg if maribavir orally, twice daily. However, in some aspects, the present disclosure recognizes that, when co-administered with certain drugs (e.g., a cytochrome P450 3A4 (CYP3A4) inducer such as carbamazepine, phenytoin, or phenobarbital, a p-glycoprotein inducer (P-gp), an immunosuppressant, an antiarrhythmic such as digoxin, ganciclovir, or valganciclovir), the dose of maribavir and/or the co-administered drug must be monitored, altered (e.g., increased or decreased), or discontinued.

In some aspects, the present disclosure demonstrates, among other things, potential drug-drug interactions with maribavir and how exposure to maribavir and/or a CYP3A4 inducer is affected. In some embodiments, the present disclosure provides methods of treating CMV infection in a patient suffering therefrom comprising:
administering a therapeutically effective amount of maribavir to the patient, wherein the patient is receiving or has received a CYP3A4 inducer prior to administration of maribavir; and
discontinuing administration of the CYP3A4 inducer prior to administration of maribavir.

In some embodiments, the present disclosure provides methods of treating CMV infection in a patient suffering therefrom comprising:
administering an initial therapeutically effective amount of maribavir to the patient, wherein the patient is receiving a CYP3A4 inducer; and
increasing the amount of maribavir administered to the patient.

In some embodiments, the present disclosure provides methods of treating CMV infection in a patient suffering therefrom comprising:
administering a therapeutically effective amount of maribavir to the patient, wherein the patient has received a CYP3A4 inducer prior to administration of maribavir.

In some embodiments, a CYP3A4 inducer is selected from the group consisting of rifampin, avasimibe, carbamazepine, phenytoin, rifabutin, phenobarbital, and St. John's wort. In some embodiments a CYP3A4 inducer decreases maribavir exposure. In some embodiments, an initial therapeutically effective amount of maribavir is administered to the patient, and the amount of maribavir is increased when co-administering a CYP3A4 inducer. In some embodiments, an initial therapeutically effective amount of maribavir is about 400 mg, orally twice daily. In some embodiments, an amount of maribavir is increased to an amount between about 800 mg and about 1200 mg, orally twice daily. In some embodiments, the provided methods further comprising a step of monitoring patient blood (e.g., whole blood or plasma) concentration of maribavir and/or the CYP3A4 inducer.

In some aspects, the present disclosure demonstrates, among other things, potential drug-drug interactions with maribavir and how exposure to maribavir and/or an immunosuppressant is affected. In some embodiments, the present disclosure provides methods of treating cytomegalovirus (CMV) infection in a patient suffering therefrom comprising administering a therapeutically effective amount of maribavir to the patient, wherein the patient is receiving or has received an immunosuppressant. In some embodiments, the immunosuppressant is selected from the group consisting of tacrolimus, cyclosporine, everolimus, sirolimus, prednisone, and mycophenolate. In some embodiments, the immunosuppressant is selected from the group consisting of tacrolimus, cyclosporine, everolimus, and sirolimus. In some embodiments, an immunosuppressant is tacrolimus. In some embodiments, provided methods further comprising the step of monitoring the levels of immunosuppressant after discontinuing administration of maribavir (e.g., with comparison to a reference or standard level). In some embodiments, provided methods further comprising the step of increasing the amount of immunosuppressant administered to the patient (e.g., to the amount of immunosuppressant that was administered prior to commencing administration of maribavir).

In some embodiments, tacrolimus is administered at an initial dose and whole blood trough concentrations are monitored. In some embodiments, an initial dose (e.g., prior to administration of maribavir or upon co-administration of maribavir) of tacrolimus administered is between about 0.075 mg/kg/day and about 0.3 mg/kg/day. In some embodiments, tacrolimus is administered orally in capsules of 0.5 mg, 1.0 mg, or 5.0 mg each. In some embodiments, tacrolimus is administered by injection in a concentration of 5.0 mg/mL. In some embodiments, tacrolimus is administered by oral suspension in 1 mg unit-dose granule packets. In some embodiments, observed whole blood trough concentration of tacrolimus is monitored over a period of time between about 0 months and about 12 months from initial administration of tacrolimus. In some embodiments, observed whole blood trough concentration of tacrolimus is monitored at initial administration, during co-administration, and at discontinuation of maribavir administration. In some embodiments, observed whole blood trough concentration of tacrolimus is between about 4 and about 20 ng/mL.

In some embodiments, tacrolimus is administered at an initial dose of between about 0.03% and about 0.1% (w/w) per gram of ointment. In some embodiments, tacrolimus is administered topically in a base selected from the group consisting of mineral oil, paraffin, propylene carbonate, white petrolatum and white wax.

In some embodiments, a dose of tacrolimus is adjusted when co-administered with maribavir. In some embodiments, maribavir is co-administered at a concentration of 400 mg, 800 mg, or 1200 mg, administered twice daily. In some embodiments, co-administration of maribavir increases exposure to tacrolimus by about 50%.

In some aspects, the present disclosure demonstrates, among other things, potential drug-drug interactions with maribavir and how exposure to maribavir and/or an antiarrhythmic (e.g., digoxin) is affected. In some embodiments, the present disclosure provides methods of treating CMV infection in a patient suffering therefrom comprising administering a therapeutically effective amount of maribavir to the patient, wherein the patient is receiving or has received an antiarrhythmic (e.g., digoxin). In some embodiments, provided methods further comprise monitoring the levels of digoxin in patient serum. In some embodiments, provided methods further comprise the step of reducing the amount of digoxin administered to the patient (e.g., to the amount of antiarrhythmic that was administered prior to commencing administration of maribavir).

In some aspects, the present disclosure demonstrates, among other things, potential drug-drug interactions with maribavir and how exposure to maribavir and/or ganciclovir or valganciclovir is affected. In some embodiments, the present disclosure provides methods of treating cytomegalovirus (CMV) infection in a patient suffering therefrom comprising:
  administering a therapeutically effective amount of maribavir to the patient, wherein the patient is receiving or has received ganciclovir or valganciclovir prior to administration of maribavir; and
  discontinuing administration of the ganciclovir or valganciclovir prior to administration of maribavir.

In some embodiments, concentration of maribavir and/or the other drug being co-administered (e.g., a CYP3A4 inducer such as carbamazepine, phenytoin, or phenobarbital, a p-glycoprotein inducer (P-gp), an immunosuppressant, an antiarrhythmic such as digoxin, ganciclovir, or valganciclovir) is monitored at initial administration, during co-administration, and at discontinuation of maribavir administration.

In some embodiments, the patient is refractory to treatment with one or more other drugs to treat CMV infection (e.g., ganciclovir, valganciclovir, cidofovir, or foscarnet). In some embodiments, maribavir is administered with or without food. In some embodiments, the patient is a transplant recipient (e.g., a hematopoietic stem cell transplant recipient or a solid organ transplant recipient). In some embodiments, the patient is an adult or a child over 12 years old and greater than 35 kg.

DETAILED DESCRIPTION

Figure 1:
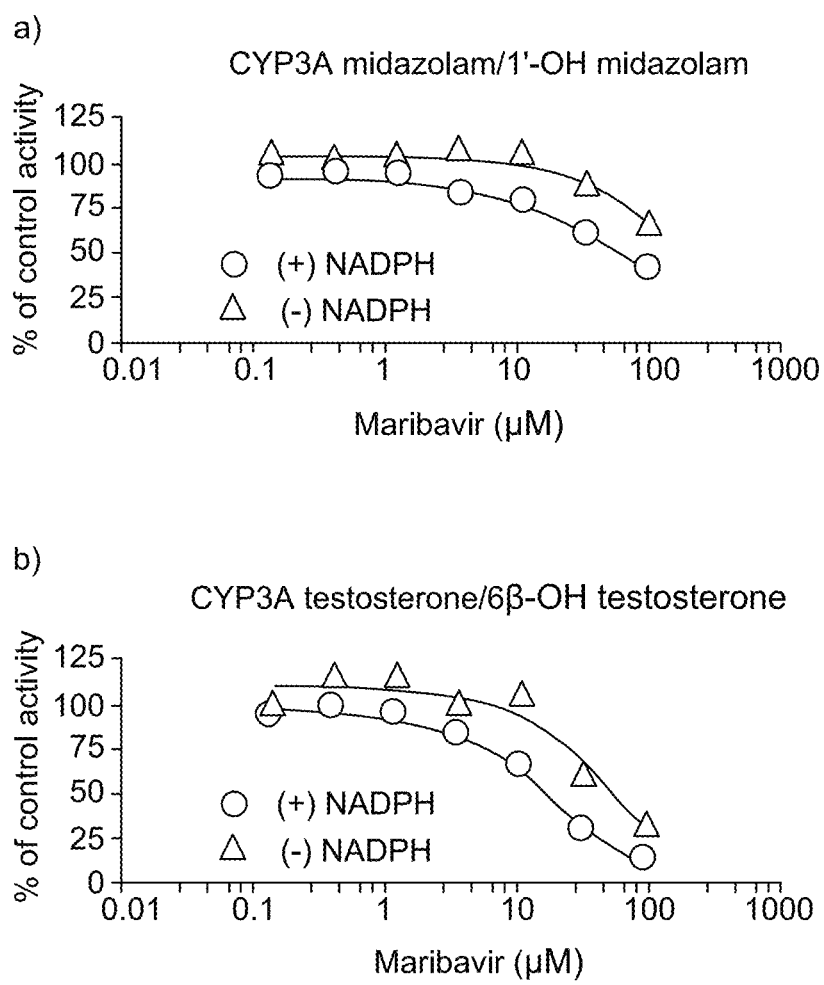
FIG. 1. $IC_{50}$ shift of maribavir in a concentration-dependent assay with HLM for CYP3A with midazolam (A) or testosterone (B) as a probe substrate. CYP, cytochrome P450; HLM, human liver microtomes; $IC_{50}$, half maximal inhibitory concentration; NADPH, nicotinamide-adenine dinucleotide phosphate.

Maribavir ((2S,3S,4R,5S)-2-(5,6-dichloro-2-(isopropylamino)-1H-benzo[d]imidazol-1-yl)-5-(hydroxymethyl)tetrahydrofuran-3,4-diol), a compound having the chemical structure:

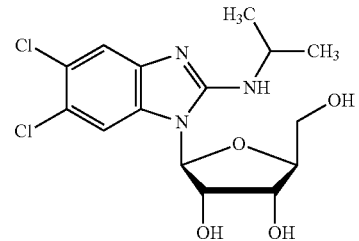

is a potent and orally bioavailable antiviral for the treatment of cytomegalovirus (CMV) infection and disease in transplant recipients. Transplant recipients are at significant risk of CMV infection and also often receive numerous concomitant medications to manage their comorbidities. Thus, evaluating the drug-drug interaction potential between maribavir and prospective therapies is useful. Further, understanding the clinical pharmacology of maribavir is necessary to define the optimal dosing strategy in transplant recipients who often have multiple comorbidities and require complex concurrent medication regimens.

1. Definitions

As used herein, the term "about," when used in reference to a numerical value, means±10% of that value. For example, a dose that comprises "about 100 mg" of maribavir encompasses any amount of maribavir within a range of 90 mg to 110 mg.

As used herein, the term "reference" describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

The terms "treat" or "treating," as used herein, refers to partially or completely alleviating, inhibiting, ameliorating and/or relieving a disorder or condition, or one or more symptoms of the disorder or condition. As used herein, the terms "treatment," "treat," and "treating" refer to partially or completely alleviating, inhibiting, ameliorating and/or relieving a disorder or condition, or one or more symptoms of the disorder or condition, as described herein. In some embodiments, treatment may be administered after one or more symptoms have developed. In some embodiments, the term "treating" includes halting the progression of a disease or disorder. Treatment may also be continued after symptoms have resolved, for example to prevent or delay their recurrence. Thus, in some embodiments, the term "treating" includes preventing relapse or recurrence of a disease or disorder.

2. Dose Regimens

In some aspects, the present disclosure recognizes that, when co-administered with certain drugs (e.g., a CYP3A4 inducer such as carbamazepine, phenytoin, or phenobarbital, a p-glycoprotein inducer (P-gp), an immunosuppressant, an antiarrhythmic such as digoxin, ganciclovir, or valganciclovir), the dose of maribavir and/or the co-administered drug must be monitored, altered (e.g., increased or decreased), or discontinued.

In some embodiments, maribavir is administered to patients at about 400 mg orally, twice daily ("standard dose"). In some embodiments, a patient has received an initial therapeutically effective amount of maribavir, e.g., prior to receiving the additional co-administered drug. In some embodiments, an initial therapeutically effective amount of maribavir is the standard dose (400 mg orally, twice daily). In some embodiments, maribavir is administered as a tablet. In some embodiments, maribavir is administered as a tablet comprising 200 mg of maribavir. In some embodiments, provided methods comprise administering maribavir to a patient with or without food.

In some embodiments, when co-administered with certain drugs (e.g., a CYP3A4 inducer such as carbamazepine, phenytoin, or phenobarbital, a p-glycoprotein inducer (P-gp), an immunosuppressant, an antiarrhythmic such as digoxin, ganciclovir, or valganciclovir), the dose of maribavir is altered (e.g., increased or decreased) from the standard dose (400 mg orally, twice daily). In some embodiments, the amount of maribavir is increased to about 800 mg or about 1200 mg orally, twice daily. In some embodiments, the amount of maribavir is increased to about 800 mg orally, twice daily. In some embodiments, the amount of maribavir is increased to about 1200 mg orally, twice daily.

In some embodiments, when co-administered with certain drugs (e.g., a CYP3A4 inducer such as carbamazepine, phenytoin, or phenobarbital, a p-glycoprotein inducer (P-gp), an immunosuppressant, an antiarrhythmic such as digoxin, ganciclovir, or valganciclovir), the dose of the co-administered drug is altered (e.g., increased or decreased) from its recommended amount provided by its label. In some embodiments, the dose of the co-administered drug is decreased as compared to its standard dosing regimen. In some embodiments, provided methods further comprising the step of monitoring the levels of a coadministered drug after discontinuing administration of maribavir (e.g., with comparison to a reference or standard level). In some embodiments, provided methods further comprising the step of increasing the amount of a coadministered drug administered to the patient (e.g., to the amount of a coadministered drug that was administered prior to commencing administration of maribavir).

a. Maribavir and CYP3A4 Inducers

In some embodiments, the present disclosure provides the recognition that maribavir is primarily metabolized by CYP3A4. Additionally or alternatively, the present disclosure provides the recognition that drugs that are CYP3A4 inducers decrease maribavir plasma concentrations and may result in a reduced virologic response. In some embodiments, coadministration of maribavir with certain CYP3A4 inducers is not recommended, and/or dosing regimens of one or both drugs should be altered.

In some embodiments, the present disclosure provides methods of treating CMV infection in a patient suffering therefrom comprising administering a therapeutically effective amount of maribavir to the patient, wherein the patient is receiving or has received a CYP3A4 inducer prior to administration of maribavir. In some embodiments, methods further comprise discontinuing administration of the CYP3A4 inducer prior to administration of maribavir. In some embodiments, method further comprise increasing the amount of maribavir administered to the patient.

In some embodiments, a CYP3A4 inducer is selected from the group consisting of rifampin, avasimibe, carbamazepine, phenytoin, rifabutin, phenobarbital, and St. John's wort. In some embodiments, a CYP3A4 inducer is selected from the group consisting of rifampin, carbamazepine, phenytoin, rifabutin, phenobarbital, and St. John's wort. In some embodiments, a CYP3A4 inducer is selected from the group consisting of rifampin, rifabutin, and St. John's wort. In some embodiments, a CYP3A4 inducer is selected from the group consisting of carbamazepine, phenytoin, and phenobarbital. In some embodiments, a CYP3A4 inducer is a strong CYP3A4 inducer. Strong CYP3A4 inducer include, e.g., rifampin, rifabutin, and St. John's wort. In some embodiments, CYP3A4 inducers may be administered in accordance with approved dosing regimens for the patient to be treated (e.g., a US FDA approved dosage for a given indication).

In some embodiments, a CYP3A4 inducer is also a p-Gp inducer. In some embodiments, a CYP3A4 inducer also decreases maribavir exposure.

In some embodiments, the present disclosure provides methods of treating CMV infection in a patient suffering therefrom comprising:
  administering a therapeutically effective amount of maribavir to the patient (e.g., 400 mg orally, twice daily), wherein the patient is receiving or has received a cytochrome P450 3A4 (CYP3A4) inducer prior to administration of maribavir; and
  discontinuing administration of the CYP3A4 inducer prior to administration of maribavir.

In some embodiments, the present disclosure provides methods of treating CMV infection in a patient suffering therefrom comprising:
  administering an initial therapeutically effective amount of maribavir to the patient (e.g., 400 mg orally, twice daily), wherein the patient is receiving a cytochrome P450 3A4 (CYP3A4) inducer; and
  increasing the amount of maribavir administered to the patient.

In some embodiments, an initial therapeutically effective amount of maribavir is the standard dose (400 mg orally, twice daily). In some embodiments, the amount of maribavir is increased to about 800 mg or about 1200 mg orally, twice daily. In some embodiments, the amount of maribavir is increased to about 800 mg orally, twice daily. In some embodiments, the amount of maribavir is increased to about 1200 mg orally, twice daily. In some embodiments, wherein the CYP3A4 inducer is carbamazepine, the amount of maribavir is increased to about 800 mg of maribavir orally twice daily. In some embodiments, wherein the CYP3 A4 inducer is phenytoin or phenobarbital, the amount of maribavir is increased to about 1200 mg of maribavir orally twice daily.

In some embodiments, the present disclosure provides methods of treating CMV infection in a patient suffering therefrom comprising:
  administering a therapeutically effective amount of maribavir to the patient (e.g., 800 mg or about 1200 mg orally, twice daily), wherein the patient has received a cytochrome P450 3A4 (CYP3A4) inducer prior to administration of maribavir.

In some embodiments, wherein the patient has received a CYP3A4 inducer prior to administration of maribavir, a therapeutically effective amount of maribavir is about 800 mg or about 1200 mg orally, twice daily. In some embodiments, wherein the CYP3 A4 inducer is carbamazepine, the amount of maribavir administered is about 800 mg orally, twice daily. In some embodiments, wherein the CYP3A4 inducer is phenytoin or phenobarbital, the amount of maribavir administered is about 1200 mg orally, twice daily.

Drug-drug interaction potential of maribavir with cytochrome P450 enzymes and P-glycoprotein (P-gp) was thoroughly characterized. The reversible inhibition, time-dependent inhibition, and induction of CYPs were evaluated in the presence of maribavir using human cells or human-derived cell lines. The inhibition of P-gp was also assessed.

Maribavir was not a reversible inhibitor of CYP2A6, CYP2B6, CYP2C8, CYP2D6, CYP2E1, or CYP3A4 but was a weak inhibitor of CYP1A2, CYP2C9, and CYP2C19 (the half maximal inhibitory concentration, or $IC_{50}$, was 40, 18, and 35 µM, respectively).

Figure 2:
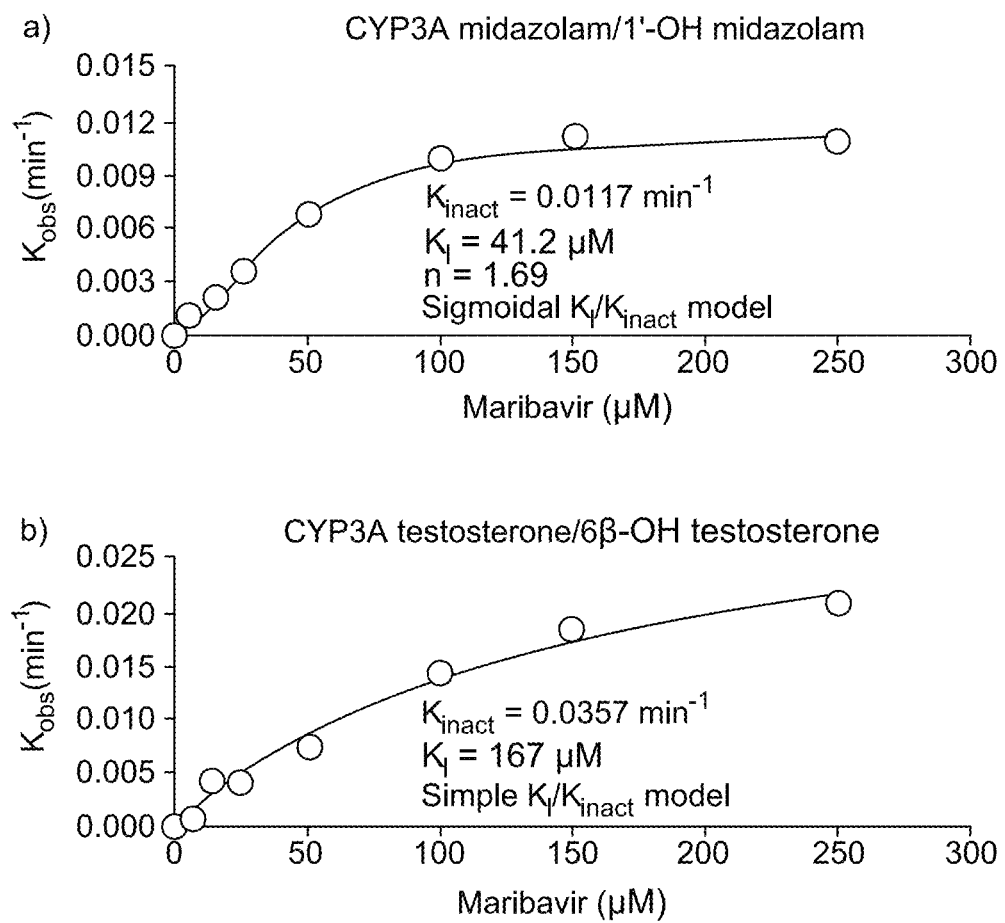
FIG. 2. Observed enzyme inactivation rate constant vs. inhibitor concentration for TDI of CYP3A by maribavir with (A) midazolam or (B) testosterone as probe substrate. CYP, cytochrome P450; $k_I$, inhibitor concentration at half maximal enzyme inactivation; $k_{inact}$, maximum enzyme inactivation rate constant; $k_{obs}$, observed enzyme inactivation rate constant; TDI, time-dependent inhibition.

Maribavir was not a time-dependent inhibitor of CYP1A2, CYP2C8, CYP2C9, CYP2C19, or CYP2D6. However, it was a time-dependent inhibitor of CYP3 A4, evident from $IC_{50}$ shift values presented in FIG. 1. With midazolam and testosterone as probe substrates, $IC_{50}$ values for maribavir were greater than 1.9 and 3.2 µM, respectively. Maribavir's concentration at half-maximal enzyme inactivation, or $k_I$, of CYP3A was 41.2 µM and 167 µM with midazolam and testosterone, respectively, as shown in FIG. 2.

Figure 3:
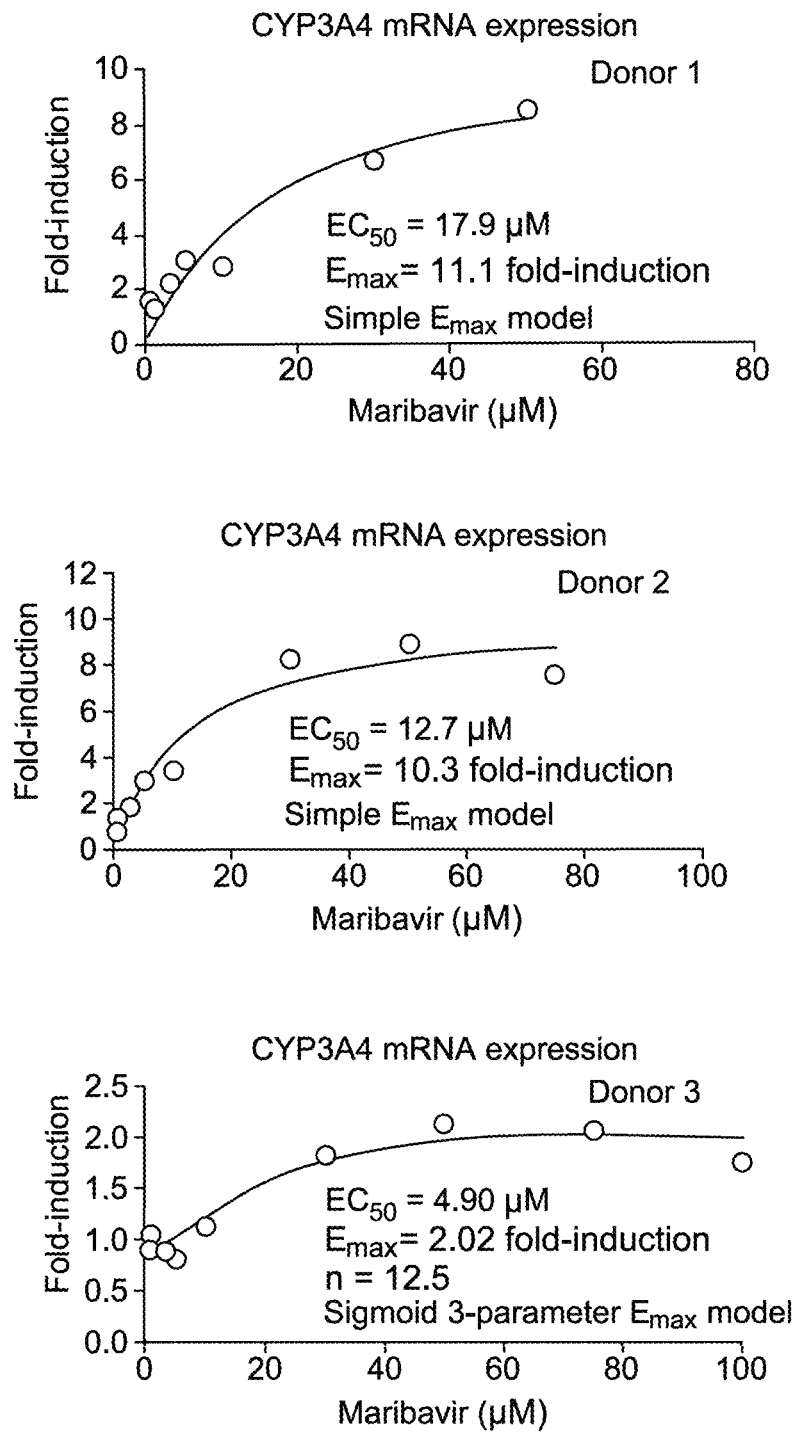
FIG. 3. Estimation of induction $E_{max}$ and $EC_{50}$ of CYP3A4 mRNA expression by maribavir through non-linear regression of data obtained from three donors of human hepatocytes. For donor 3, n is the sigmoidicity coefficient that accommodates the shape of the curve; $EC_{50}$, half maximal effective concentration; $E_{max}$, maximum effect.

Maribavir was not an inducer of CYP1A2 or CYP2B6 mRNA, but was a weak in vitro inducer for CYP3A4 mRNA, exhibiting a greater than 14-fold increase in mRNA induction and a greater than 30% increase in positive control levels. However, effects varied across donors, as FIG. 3 shows. The half-maximal effective concentration, or $EC_{50}$, of maribavir was greater than 5 µM for all donors.

Figure 4:
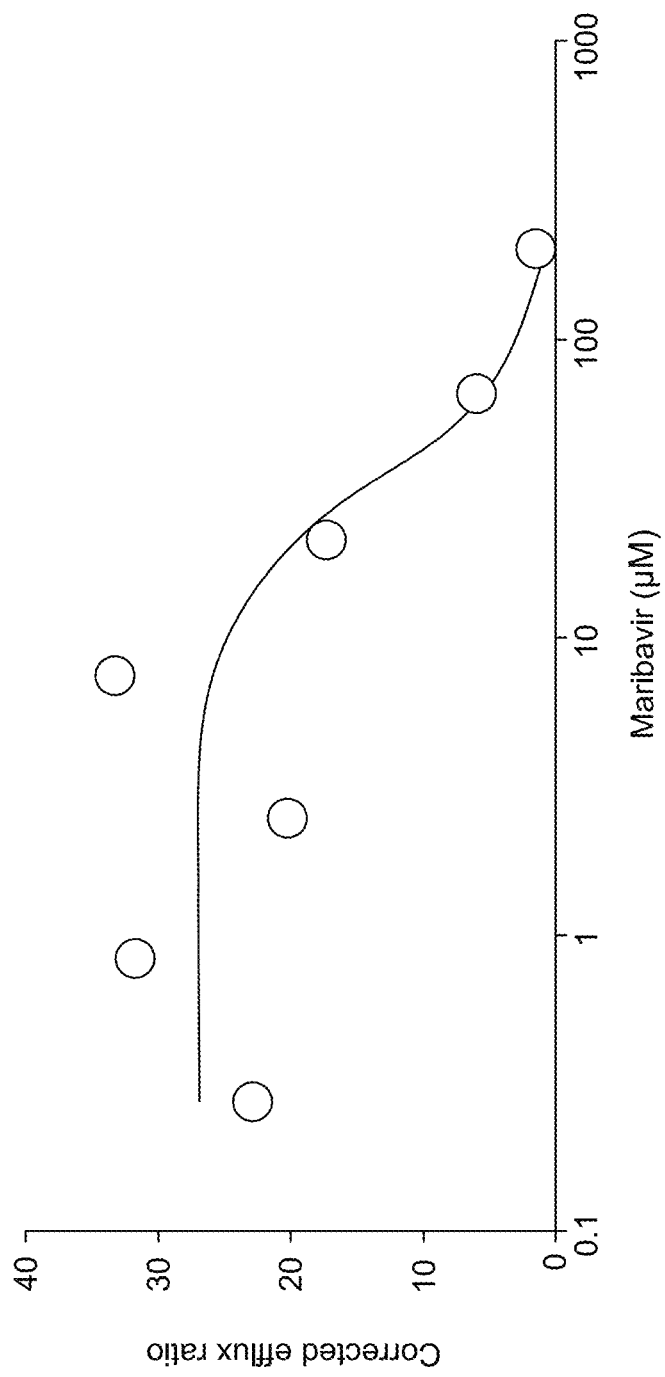
FIG. 4. Estimation of $IC_{50}$ of maribavir on P-gp efflux of digoxin (as determined by the corrected efflux ratio) in cultured Caco-2 cells. $IC_{50}$, half maximal inhibitory concentration; P-gp, P-glycoprotein.

As shown in FIG. 4, maribavir demonstrated concentration-dependent inhibition of P-gp-mediated digoxin efflux. The $IC_{50}$ of maribavir in this case was 33.8 µM.

The data presented herein, specifically in Example 1, demonstrate the concentrations of maribavir required for the observed levels of in vitro inhibition or induction of P-gp and/or some CYPs.

b. Maribavir and Immunosuppressants

In some embodiments, the present disclosure recognizes that maribavir has the potential to increase the drug concentrations of certain immunosuppressant drugs that are CYP3A4 and/or P-gp substrates, where minimal concentration changes may lead to serious adverse events. Additionally or alternatively, immunosuppressant drug levels should be frequently monitored through treatment with maribavir, and especially following initiation and after discontinuation of maribavir, and adjust the immunosuppressant dose, as needed.

In some embodiments, the present disclosure provides methods of treating CMV infection in a patient suffering therefrom comprising administering a therapeutically effective amount of maribavir to the patient (e.g., 400 mg orally, twice daily), wherein the patient is receiving or has received an immunosuppressant. In some embodiments, methods further comprise monitoring the levels of immunosuppressant (e.g., in whole blood or plasma). In some embodiments, methods further comprise reducing the amount of immunosuppressant administered to a patient. In some embodiments, maribavir also increases immunosuppressant exposure. In some embodiments, provided methods further comprise the step of monitoring the levels of immunosuppressant after discontinuing administration of maribavir (e.g., with comparison to a reference or standard level). In some embodiments, provided methods further comprise the step of increasing the amount of immunosuppressant administered to the patient (e.g., to the amount of immunosuppressant that was administered prior to commencing administration of maribavir).

In some embodiments, an immunosuppressant is selected from the group consisting of tacrolimus, cyclosporine, everolimus, sirolimus, prednisone, and mycophenolate. In some embodiments, an immunosuppressant is selected from the group consisting of tacrolimus, cyclosporine, everolimus, and sirolimus. In some embodiments, an immunosuppressant is tacrolimus. In some embodiments, an immunosuppressant is selected from the group consisting of tacrolimus, cyclosporine, everolimus, prednisone, and mycophenolate. In some embodiments, an immunosuppressant is tacrolimus. In some embodiments, an immunosuppressant is everolimus. In some embodiments, an immunosuppressant is cyclosporine. In some embodiments, an immunosuppressant is sirolimus.

In some embodiments, immunosuppressants may be administered in accordance with approved dosing regimens for the patient to be treated (e.g., a US FDA approved dosage for tacrolimus). In some embodiments, tacrolimus is administered as a stable dose, twice daily, with a total daily dose between about 0.5 mg and about 16 mg.

In some embodiments, tacrolimus is administered at an initial dose and whole blood trough concentrations are monitored. In some embodiments, an initial dose (e.g., prior to administration of maribavir or upon co-administration of maribavir) of tacrolimus administered is between about 0.075 mg/kg/day and about 0.3 mg/kg/day. In some embodiments, tacrolimus is administered orally in capsules of 0.5 mg, 1.0 mg, or 5.0 mg each. In some embodiments, tacrolimus is administered by injection in a concentration of 5.0 mg/mL. In some embodiments, tacrolimus is administered by oral suspension in 1 mg unit-dose granule packets. In some embodiments, observed whole blood trough concentration of tacrolimus is monitored over a period of time between about 0 months and about 12 months from the initial administration of tacrolimus. In some embodiments, observed whole blood trough concentration of tacrolimus is monitored at initial administration, during co-administration, and at discontinuation of maribavir administration. In some embodiments, observed whole blood trough concentration of tacrolimus is between about 4 and about 20 ng/mL. In some embodiments, an initial dose of tacrolimus administered is between about 0.03% and about 0.1% (w/w) per gram of ointment. In some embodiments, tacrolimus is administered topically in a base selected from the group consisting of mineral oil, paraffin, propylene carbonate, white petrolatum and white wax. In some embodiments, co-administration of maribavir increases exposure to tacrolimus by about 50%.

In some embodiments, the present disclosure provides methods of administering to a patient in need thereof a therapeutically effective amount of an immunosuppressant for the prophylaxis or treatment of organ rejection and/or graft versus host disease, the improvement comprising administering a therapeutically effective amount of maribavir to the patient. In some embodiments, the improvement further comprises a step of reducing the amount of immunosuppressant received. In some embodiments, the improvement further comprises a step of reducing the amount of immunosuppressant received, wherein the immunosuppressant is tacrolimus.

In some embodiments, the present disclosure provides methods for prophylaxis or treatment of organ rejection and/or graft versus host disease a patient in need thereof, wherein the patient is receiving or has received a therapeutically effective amount of an immunosuppressant, the improvement comprising administering a therapeutically effective amount of maribavir to the patient. In some embodiments, the improvement further comprises a step of reducing the amount of immunosuppressant received. In some embodiments, the improvement further comprises a step of reducing the amount of immunosuppressant received, wherein the immunosuppressant is tacrolimus.

In some embodiments, the present disclosure provides methods for prophylaxis or treatment of organ rejection and/or graft versus host disease a patient in need thereof, wherein the patient is receiving or has received a therapeutically effective amount of maribavir, the improvement comprising administering a therapeutically effective amount of an immunosuppressant to the patient. In some embodiments, the improvement further comprises a step of reducing the amount of immunosuppressant received. In some embodiments, the improvement further comprises a step of reducing the amount of immunosuppressant received, wherein the immunosuppressant is tacrolimus.

c. Maribavir and Digoxin

Digoxin is an antiarrhythmic drug most frequently used for atrial fibrillation, atrial flutter, and heart failure. In some embodiments, the present disclosure recognizes that maribavir has the potential to increase the drug concentrations of digoxin, which is a P-gp substrate, where minimal concentration changes may lead to serious adverse events. Additionally or alternatively, digoxin levels should be frequently monitored through treatment with maribavir, and especially following initiation and after discontinuation of mariabavir, and adjust the immunosuppressant dose, as needed.

In some embodiments, the present disclosure provides methods of treating cytomegalovirus (CMV) infection in a patient suffering therefrom comprising administering a therapeutically effective amount of maribavir to the patient, wherein the patient is receiving or has received digoxin. In some embodiments, provided methods further comprise monitoring the levels of digoxin (e.g., in whole blood or plasma). In some embodiments, provided methods further comprise reducing the amount of digoxin administered to a patient, e.g., as compared to the amount prior to co-administering maribavir, such as the US FDA approved dosage. In some embodiments, digoxin is administered as 0.5 mg, once daily.

d. Maribavir and Ganciclovir or Valganciclovir

In some embodiments, the present disclosure recognizes that maribavir may antagonize the antiviral activity of ganciclovir and/or valganciclovir by inhibiting human CMV pUL97 kinase, which is required for activation/phosphorylation of ganciclovir and valganciclovir.

In some embodiments, the present disclosure provides methods of treating cytomegalovirus (CMV) infection in a patient suffering therefrom comprising administering a therapeutically effective amount of maribavir to the patient, wherein the patient is receiving or has received ganciclovir and/or valganciclovir. In some embodiments, provided methods further comprise discontinuing administration of ganciclovir and/or valganciclovir prior to administration of maribavir. In some embodiments, provided methods further comprising the step of monitoring the levels of ganciclovir and/or valganciclovir (e.g., in whole blood or plasma) after discontinuing administration of maribavir (e.g., with comparison to a reference or standard level). In some embodiments, provided methods further comprising the step of increasing the amount of ganciclovir and/or valganciclovir administered to the patient (e.g., to the amount of ganciclovir and/or valganciclovir that was administered prior to commencing administration of maribavir).

3. Patients

As described above and herein, the present methods provide administering maribavir and a co-administered drug (e.g., a CYP3A4 inducer such as carbamazepine, phenytoin, or phenobarbital, a p-glycoprotein inducer (P-gp), an immunosuppressant, an antiarrhythmic such as digoxin, ganciclovir, or valganciclovir) to a patient in need thereof. In some embodiments, a patient suffers from CMV infection. In some embodiments, a patient suffers from post-transplant CMV infection. In some embodiments, a patient is a transplant recipient. In some embodiments, a patient is a hematopoietic stem cell transplant recipient. In some embodiments, a patient is a solid organ transplant recipient (e.g., liver, kidney, lung, heart, pancreas, intestine).

In some embodiments, a patient is refractory to treatment with one or more other drugs to treat CMV infection. In some embodiments, a patient is refractory with genotypic resistance to treatment with one or more other drugs to treat CMV infection. In some embodiments, a patient is refractory without genotypic resistance to treatment with one or more other drugs to treat CMV infection. In some embodiments, a patient is refractory to treatment with one or more of ganciclovir, valganciclovir, cidofovir, or foscarnet. In some embodiments, a patient is refractory to treatment with ganciclovir or valganciclovir. In some embodiments, a patient is refractory to treatment with ganciclovir. In some embodiments, a patient is refractory to treatment with valganciclovir.

In some embodiments, a patient is an adult or a child over 12 years old and greater than 35 kg. In some embodiments, a patient is an adult. In some embodiments, a patient is a child. In some embodiments, a patient is a child over 12 years old. In some embodiments, a patient is a child over 35 kg. In some embodiments, a patient is a child over 12 years old and over 35 kg.

4. Evaluating Maribavir Drug-Drug Interaction Potential Using Data from Phase 1 Clinical Studies and Nonclinical In Vitro Studies Maribavir's drug-drug interaction potential are described in Example 3.

Accumulated data have shown that maribavir is metabolized primarily in the liver, and renal clearance is a minor route (representing less than 5 percent). VP 44469 (N-dealkylated Maribavir) was the principal metabolite of maribavir in both urine and feces. In plasma, unchanged maribavir and VP 44469 represented approximately 69% and 9.8% of total radioactivity, respectively. The hepatic metabolism of maribavir was primarily driven by cytochrome P450s. CYP3A4 and CYP1A2 were responsible for 70 to 85% and 15 to 30% of the CYP-driven pathways, respectively. Glucuronidation accounted for less than 20% of metabolism.

Clinically significant drug interactions are summarized in Table 1-A of Example 3. Potent inducers of CYP34A and P-gp decrease maribavir exposure, necessitating maribavir dose increases. Inhibitors of CYP3 A4 and/or P-gp may increase maribavir exposure. However, previous safety and tolerability data indicate that dose reduction is not necessary with CYP3A4 and/or P-gp inhibitors. Maribavir may increase the exposure of immunosuppressants, so monitoring of concomitant immunosuppressants should be considered.

5. Clinical Pharmacology of Maribavir

Following oral administration, maribavir was rapidly and well absorbed, with peak concentrations generally achieved within 1 to 3 hours; exposure was unaffected by food; and bioavailability wasn't affected by crushing the tablet or when it was taken with antacids.

Maribavir was metabolized in the liver through the cytochrome P450 3A4 and 1A2 pathways. Less than 5 percent of maribavir was eliminated through the kidneys. Maribavir demonstrated a half-life of approximately 5 to 7 hours.

Maribavir was found to present a low risk for drug-to-drug interactions. Co-administration of potent CYP3A4 inducers was found to decrease the exposure of maribavir, necessitating a maribavir dose increase. Some immunosuppressants, such as tacrolimus, may be affected by maribavir, which increased tacrolimus exposure by 51%.

In conclusion, maribavir is a suitable treatment for CMV infections in a broad range of transplant recipients. It can be taken with or without food, and no dose adjustment is needed in patients with mild-to-moderate hepatic impairment or renal impairment. Maribavir has a low drug-interaction potential and there are minimal dose adjustments required (for example, only when taken concurrently with CYP3 A4 inducers or certain immunosuppressants) and there are no effects on QT interval.

Exemplary Embodiments

The following numbered embodiments, while non-limiting, are exemplary of certain aspects of the present disclosure:

1 A method of treating cytomegalovirus (CMV) infection in a patient suffering therefrom comprising:
administering a therapeutically effective amount of maribavir to the patient, wherein the patient is receiving or has received a cytochrome P450 3A4 (CYP3A4) inducer prior to administration of maribavir; and
discontinuing administration of the CYP3A4 inducer prior to administration of maribavir.

2. The method of embodiment 1, wherein the CYP3 A4 inducer is selected from the group consisting of rifampin, avasimibe, carbamazepine, phenytoin, rifabutin, phenobarbital, and St. John's wort.

3. The method of embodiments 1 or 2, wherein the CYP3A4 inducer is a strong CYP3A4 inducer.

4. The method of any one of embodiments 1-3, wherein the CYP3A4 inducer is selected from the group consisting of rifampin, rifabutin, and St. John's wort.

5. The method of any one of embodiments 1-4, comprising administering about 400 mg of maribavir orally to the patient twice daily.

6. The method of any one of embodiments 1-5, comprising administering maribavir to the patient with or without food.

7. A method of treating cytomegalovirus (CMV) infection in a patient suffering therefrom comprising:
administering an initial therapeutically effective amount of maribavir to the patient, wherein the patient is receiving a cytochrome P450 3A4 (CYP3A4) inducer; and
increasing the amount of maribavir administered to the patient.

8. The method of embodiment 7, wherein the CYP3 A4 inducer is selected from the group consisting of rifampin, avasimibe, carbamazepine, phenytoin, rifabutin, phenobarbital, and St. John's wort.

9. The method of embodiment 7 or 8, wherein the CYP3A4 inducer is selected from the group consisting of rifampin, carbamazepine, phenytoin, rifabutin, phenobarbital, and St. John's wort.

10. The method of any one of embodiments 7-9, wherein the CYP3A4 inducer is selected from the group consisting of carbamazepine, phenytoin, and phenobarbital.

11. The method of any one of embodiments 7-10, wherein the patient had received a therapeutically effective amount of maribavir prior to receiving a CYP3A4 inducer ("an initial therapeutically effective amount") of about 400 mg of maribavir orally twice daily.

12. The method of any one of embodiments 7-11, wherein the amount of maribavir is increased to about 800 or about 1200 mg of maribavir orally twice daily.

13. The method of any one of embodiments 7-12, wherein the CYP3A4 inducer is carbamazepine, and the amount of maribavir is increased to about 800 mg of maribavir orally twice daily.

14. The method of any one of embodiments 7-12, wherein the CYP3A4 inducer is phenytoin or phenobarbital, and the amount of maribavir is increased to about 1200 mg of maribavir orally twice daily.

15. A method of treating cytomegalovirus (CMV) infection in a patient suffering therefrom comprising:
administering a therapeutically effective amount of maribavir to the patient, wherein the patient has received a cytochrome P450 3A4 (CYP3A4) inducer prior to administration of maribavir.

16. The method of embodiment 15, wherein the CYP3A4 inducer is selected from the group consisting of rifampin, avasimibe, carbamazepine, phenytoin, rifabutin, phenobarbital, and St. John's wort.

17. The method of embodiment 15 or 16, wherein the CYP3A4 inducer is selected from the group consisting of rifampin, carbamazepine, phenytoin, rifabutin, phenobarbital, and St. John's wort.

18. The method of any one of embodiments 15-17, wherein the CYP3A4 inducer is selected from the group consisting of carbamazepine, phenytoin, and phenobarbital.

19. The method of any one of embodiments 15-18, wherein the amount of maribavir administered is about 800 or about 1200 mg orally twice daily.

20. The method of any one of embodiments 15-19, wherein the CYP3A4 inducer is carbamazepine, and the amount of maribavir administered is about 800 mg orally twice daily.

21. The method of any one of embodiments 15-19, wherein the CYP3A4 inducer is phenytoin or phenobarbital, and the amount of maribavir administered is about 1200 mg orally twice daily.

22. The method of any one of embodiments 1-21, wherein the CYP3A4 inducer decreases maribavir exposure.

23. A method of treating cytomegalovirus (CMV) infection in a patient suffering therefrom comprising administering a therapeutically effective amount of maribavir to the patient, wherein the patient is receiving or has received an immunosuppressant.

24. The method of embodiment 23, further comprising the step of monitoring the levels of immunosuppressant after commencing administration of Maribavir (e.g., with comparison to a reference or standard level).

25. The method of embodiment 23 or 24, further comprising the step of reducing the amount of the immunosuppressant administered to the patient.

26. The method of any one of embodiments 23-25, further comprising the step of monitoring the levels of immunosuppressant after discontinuing administration of maribavir (e.g., with comparison to a reference or standard level).

27. The method of embodiment 26, further comprising the step of increasing the amount of immunosuppressant administered to the patient (e.g., to the amount of immunosuppressant that was administered prior to commencing administration of maribavir).

28. The method of any one of embodiments 23-27, wherein immunosuppressant is selected from the group consisting of tacrolimus, cyclosporine, everolimus, sirolimus, prednisone, and mycophenolate.

29. The method of any one of embodiments 23-28, wherein immunosuppressant is selected from the group consisting of tacrolimus, cyclosporine, everolimus, and sirolimus.

30. A method of treating cytomegalovirus (CMV) infection in a patient suffering therefrom comprising administering a therapeutically effective amount of maribavir to the patient, wherein the patient is receiving or has received digoxin.

31. The method of embodiment 30, further comprising the step of monitoring the levels of digoxin.

32. The method of embodiment 30 or 31, further comprising the step of reducing the amount of the digoxin administered to the patient.

33. The method of one of embodiments 1-32, wherein the patient is refractory to treatment with one or more other drugs to treat CMV infection.

34. The method of one of embodiments 1-33, wherein the patient is refractory to treatment with one or more of ganciclovir, valganciclovir, cidofovir, or foscarnet.

35. The method of any one of embodiments 1-34, wherein the patient is refractory to treatment with genotypic resistance.

36. The method of any one of embodiments 1-34, wherein the patient is refractory to treatment without genotypic resistance.

37. A method of treating cytomegalovirus (CMV) infection in a patient suffering therefrom comprising:
administering a therapeutically effective amount of maribavir to the patient, wherein the patient is receiving or has received ganciclovir or valganciclovir prior to administration of maribavir; and
discontinuing administration of the ganciclovir or valganciclovir prior to administration of maribavir.

38. The method of any one of embodiments 7-37, comprising administering maribavir to the patient with or without food.

39. The method of any one of embodiments 1-38, wherein the patient is a transplant recipient.

40. The method of any one of embodiments 1-39, wherein the patient is a hematopoietic stem cell transplant recipient.

41. The method of any one of embodiments 1-39, wherein the patient is a solid organ transplant recipient.

42. The method of any one of embodiments 1-41, wherein the patient is an adult or a child over 12 years old and greater than 35 kg.

EXAMPLES

Example 1—In Vitro Profiling for Potential Cytochrome P450 Drug-Drug Interaction by Maribavir Inhibition or induction of the cytochrome P450 enzymes (CYPs) are among the most commonly observed mechanisms of drug-drug interactions.

In vitro systems such as human liver microsomes (HLM), recombinant enzymes, human hepatocytes, and other human-derived cells lines have long been used as validation systems for characterization of potential drug-drug interactions prior to clinical studies.

Reversible CYP Inhibition

HLM were used to evaluate maribavir's half maximal inhibitory concentration ($IC_{50}$) on inhibition of activities of nine CYP isoforms. Probe substrates were phenacetin (CYP1A2), coumarin (CYP2A6), bupropion (CYP2B6), paclitaxel (CYP2C8), tolbutamide (CYP2C9), (S)-mephenytoin (CYP2C19), dextromethorphan (CYP2D6), clorzoxazone (CYP2E1), and midazolam and testosterone (CYP3A4).

CYP activities with 0, 0.1, 0.3, 1, 3, 10, 30, and 100 µM of maribavir were evaluated.

Incubation of maribavir in HLM at up to 100 M resulted in no significant inhibition of CYP2A6, CYP2B6, CYP2C8, CYP2D6, CYP2E1, and CYP3A4. Maribavir is a weak inhibitor of CYP1A2, CYP2C9, and CYP2C19 with ICso of 40, 18, and 35 µM, respectively.

Time-Dependent CYP Inhibition

Time-dependent inhibition (TDI) potentials for various CYP enzymes were evaluated by a 30 minute pre-incubation of maribavir with HLM in the presence and absence of nicotinamide-adenine dinucleotide diphosphate (NADPH) followed by a CYP enzyme activity assay.

Enzyme inactivation kinetics of maribavir for the TDI of CYP3A, with midazolam and testosterone as probe substrates, was evaluated by pre-incubation of HLM with maribavir at various concentrations with NADPH for six different pre-incubation time frames. CYP3A activity was measured by determining the formation of CYP3A probe metabolite.

Inhibitor concentration at half maximal enzyme inactivation ($k_1$), and maximum enzyme inactivation rate constant ($k_{inact}$), were estimated using non-linear least-square regression.

The $IC_{50}$ shift values of maribavir were <1 µM for CYP1A2, CYP2C8, CYP2C9, CYP2C19, and CYP2D6 in HLM. The $IC_{50}$ shift values of maribavir for CYP3A were greater than 1.9 and 3.2 µM, with midazolam and testosterone as probe substrate, respectively (FIG. 1). Therefore, maribavir, in concentrations of up to 100 µM, is unlikely a TDI of CYP1A2, CYP2C8, CYP2C9, CYP2C19, or CYP2D6; but it is likely a TDI of CYP3A.

$k_1$ and $k_{intact}$ of maribavir for TDI of CYP3A with midazolam as substrate (FIG. 2A) were 41.2 µM and 0.0117 min-1, respectively, $k_1$ and $k_{intact}$ of maribavir for TDI of CYP3A with testosterone as a substrate (FIG. 2B) were 167 µM and 0.0357 min-1, respectively.

CYP Induction

Fresh human hepatocytes were treated with culture medium with maribavir concentrations of 36 µM, 144 µM, and 480 µM.

Positive controls were 50 µM omeprazole (CYP1A2), 1 mM phenobarbital (CYP2B6), and 50 µM rifampicin (CYP3A).

Incubation was conducted at 37° C. for 72 hours, with daily replacement of medium with compound. Total RNA was isolated, and cDNA was synthesized from up to 1 µg of total isolated RNA. Analysis of CYP expression was performed using qPCR with CYP-specific probes.

Half maximal effective concentration ($EC_{50}$) and maximum effect ($E_{max}$) values for CYP3A4 mRNA induction were further determined by a concentration-response curve in three donors with maribavir at a concentration between 0-100 µM.

Maribavir displayed varying degrees of CYP1A2 and CYP2B6 mRNA induction in human hepatocytes. The fold-increase in mRNA was not concentration-dependent, it was variable among donors, and it did not exceed 11% of the levels of positive controls. Therefore, maribavir is likely not an inducer of CYP1A2 or of CYP2B6 mRNA at clinically relevant concentrations.

At 36 µM, maribavir displayed a greater than 14-fold increase in CYP3A4 mRNA induction and greater than 30% of positive control (rifampicin) levels. The $EC_{50}$ and $E_{max}$ values for CYP3A4 induction were then further determined by a concentration-response curve in three donors.

Maribavir also displayed donor-dependent induction of CYP3A4 mRNA upon determination of its induction $E_{max}$ and $EC_{50}$ properties (FIG. 3).

Example 2—Quantitative Prediction of Exposure of Maribavir Using Prior In Vitro and In Vivo Data A Physiologically-based Pharmacokinetic ("PBPK") model based on prior in vitro and in vivo information on the metabolism and kinetics of maribavir was constructed with the aim of predicting plasma concentration-time profiles of maribavir and to evaluate the likely impact of coadministration of CYP3 A4 inhibitors and inducers on the kinetics of maribavir in healthy subjects.

Model Development

A combination of in vitro data and clinical pharmacokinetic data obtained following a single dose of 400 mg maribavir were used to develop the PBPK model. Mean concentrations for the total virtual population (n=100) are displayed, and associated mean $C_{max}$ and $AUC_{(0-\infty)}$ values are compared in Table 2A. In addition, the predicted mean maribavir AUC values were within 1.25-fold of the observed data. The $C_{max}$ was marginally under predicted, which could be expected because the PBPK model was optimized for better prediction of $C_{12h}$.

TABLE 2A

Predicted and Observed $C_{max}$ and $AUC_{(0-\infty)}$ values for maribavir after a single oral dose of maribavir (400 mg).

| | $AUC_{(0-\infty)}$ mg/L*h | $C_{max}$ mg/L |
|---|---|---|
| PREDICTED | | |
| Mean | 97.98 | 11.98 |
| Median | 91.97 | 11.48 |
| Geometric Mean | 90.40 | 11.56 |
| 90% CI around geometric mean (lower limit) | 84.45 | 11.06 |
| 90% CI around geometric mean (upper limit) | 96.76 | 12.08 |
| $5^{th}$ percentile | 46.52 | 7.61 |
| $95^{th}$ percentile | 165.11 | 18.08 |
| SD | 39.33 | 3.26 |
| % CV | 40 | 27 |
| OBSERVED | | |
| Mean | 97.8 | 16.7 |
| SD | 28.6 | 5.72 |
| % CV | 29.2 | 34.3 |
| RATIO MEAN PREDICTED/OBSERVED | 1.00 | 0.72 |

A renal clearance of 0.051 L/H was obtained following oral administration of 50 mg to 1600 mg single doses of maribavir. In vitro human liver microsomal and recombinant CYP data combined with oral clearance values reported from two studies (n=46 individuals; Ma et al., 2006) were used to assign the relative contribution of CYP3A4 to the clearance of maribavir. Distribution models evaluated included a full PBPK model and a minimal PBPK model, both of which consider liver and intestinal metabolism. Mass balance data from the [$^{14}C$] ADME study indicated a fraction absorbed of 0.83 or greater following oral administration of 400 mg dose of maribavir. Absorption models evaluated included a simple first-order absorption model and a more mechanistic "Advanced Dissolution Absorption and Metabolism" (ADAM) model. Although maribavir has been shown to be a P-gp substrate in vitro, relatively linear pharmacokinetics across the dose range of interest, (400 mg to 1600 mg) informed the selection of the simpler first order absorption model for the use in this PBPK study.

Model Verification

A comparison of observed and predicted plasma concentrations of maribavir following single oral doses of 800 mg and 1600 mg to healthy patients were. Mean concentrations for the total virtual population (n=100) are displayed, and associated mean $C_{max}$ and $AUC_{(0-\infty)}$ values are compared in Tables 3A and 4A. The simulated and observed maribavir concentrations were in reasonable agreement. In addition, the predicted mean maribavir AUC values were within 1.25-fold of the observed data.

TABLE 3A

Predicted and Observed $C_{max}$ and $AUC_{(0-\infty)}$ values for maribavir after a single oral dose of maribavir (800 mg).

| | $AUC_{(0-\infty)}$ mg/L*h | $C_{max}$ mg/L |
|---|---|---|
| PREDICTED | | |
| Mean | 195.71 | 24.05 |
| Median | 179.48 | 23.22 |
| Geometric Mean | 180.00 | 23.23 |
| 90% CI around geometric mean (lower limit) | 167.95 | 22.23 |
| 90% CI around geometric mean (upper limit) | 192.91 | 24.27 |
| $5^{th}$ percentile | 93.03 | 15.22 |
| $95^{th}$ percentile | 330.22 | 36.17 |

TABLE 3A-continued

Predicted and Observed $C_{max}$ and $AUC_{(0-\infty)}$ values for maribavir after a single oral dose of maribavir (800 mg).

|  | $AUC_{(0-\infty)}$ mg/L*h | $C_{max}$ mg/L |
|---|---|---|
| SD | 80.04 | 6.47 |
| % CV | 41 | 27 |
| OBSERVED |  |  |
| Mean | 183 | 26.4 |
| SD | 69.1 | 6.85 |
| % CV | 38.0 | 26.0 |
| RATIO MEAN PREDICTED/OBSERVED | 1.07 | 0.91 |

TABLE 4A

Predicted and Observed $C_{max}$ and $AUC_{(0-\infty)}$ values for maribavir after a single oral dose of maribavir (1600 mg).

|  | $AUC_{(0-\infty)}$ mg/L*h | $C_{max}$ mg/L |
|---|---|---|
| PREDICTED |  |  |
| Mean | 391.43 | 48.10 |
| Median | 358.95 | 46.45 |
| Geometric Mean | 359.99 | 46.45 |
| 90% CI around geometric mean (lower limit) | 335.89 | 44.46 |
| 90% CI around geometric mean (upper limit) | 385.82 | 48.54 |
| $5^{th}$ percentile | 186.06 | 30.44 |
| $95^{th}$ percentile | 660.44 | 72.34 |
| SD | 106.09 | 12.94 |
| % CV | 41 | 27 |
| OBSERVED |  |  |
| Mean | 437 | 48.8 |
| SD | 163 | 7.88 |
| % CV | 37.4 | 16.1 |
| RATIO MEAN PREDICTED/OBSERVED | 0.90 | 0.99 |

A comparison of observed and predicted plasma concentrations of maribavir following multiple oral 400 mg BID doses of maribavir was performed. Mean concentrations for the total virtual population (n=150) are displayed, and associated mean $C_{max}$ and $AUC_{(0-\infty)}$ values are compared in Table 5A. The simulated and observed maribavir concentrations were in reasonable agreement. In addition, the predicted mean maribavir AUC values were within 1.25-fold of the observed data.

TABLE 5A

Predicted and Observed $C_{12\,h}$, $C_{max}$ and $AUC_{(0-\infty)}$ values for maribavir after multiple oral dose of maribavir (400 mg BBID, 5 doses).

|  | $AUC_{(0-\infty)}$ mg/L*h | $C_{max}$ mg/L | $C_{12\,h}$ mg/L |
|---|---|---|---|
| PREDICTED |  |  |  |
| Mean | 96.49 | 14.31 | 2.99 |
| Median | 90.13 | 14.05 | 2.44 |
| Geometric Mean | 89.31 | 13.78 | 2.13 |
| 90% CI around geometric mean (lower limit) | 85.01 | 13.31 | 1.89 |
| 90% CI around geometric mean (upper limit) | 93.82 | 14.26 | 2.15 |
| $5^{th}$ percentile | 46.35 | 8.80 | 0.36 |
| $95^{th}$ percentile | 162.88 | 20.59 | 7.76 |
| SD | 37.93 | 3.96 | 2.2 |
| % CV | 39 | 28 | 73 |
| OBSERVED |  |  |  |
| Mean | 89.9 | 16.9 | 2.54 |
| SD | 24.5 | 5.22 | 1.37 |
| % CV | 27.2 | 30.8 | 53.8 |
| RATIO MEAN PREDICTED/OBSERVED | 1.07 | 0.85 | 1.18 |

A comparison of observed and predicted plasma concentrations of maribavir following a single oral dose of 400 mg administered in the absence of ketoconazole (a CYP3A4 inhibitor) and 1 hour after a single 400 mg dose of ketoconazole to healthy subjects was performed. Mean simulated and observed plasma maribavir concentrations are compared, and associated geometric mean $C_{max}$ and $AUC_{(0-\infty)}$ values for maribavir in the presence and absence of ketoconazole are shown in Table 6A and are within 1.25-fold of the observed data.

TABLE 6A

Simulated and observed PK parameters and geometric mean $C_{max}$ and $AUC_{(0-\infty)}$ ratios for maribavir following a single oral dose of maribavir in the presence and absence of ketoconazole with associated variability in healthy adults.

|  | Maribavir | | Maribavir + Ketoconazole | | Ratio | |
|---|---|---|---|---|---|---|
|  | $AUC_{(0-\infty)}$ mg/L*h | $C_{max}$ mg/L | $AUC_{(0-\infty)}$ mg/L*h | $C_{max}$ mg/L | $AUC_{(0-\infty)}$ | $C_{max}$ |
| PREDICTED | | | | | | |
| Mean | 98.96 | 12.27 | 150.60 | 14.31 | 1.54 | 1.17 |
| Median | 93.51 | 11.91 | 140.38 | 13.75 | 1.49 | 1.15 |
| Geometric Mean | 92.29 | 11.81 | 141.16 | 13.77 | 1.53 | 1.17 |
| 90% CI around geometric mean (lower limit) | 88.30 | 11.43 | 135.28 | 13.32 | 1.51 | 1.16 |
| 90% CI around geometric mean (upper limit) | 96.45 | 12.20 | 147.30 | 14.23 | 1.55 | 1.17 |
| $5^{th}$ percentile | 48.52 | 7.50 | 77.98 | 8.85 | 1.27 | 1.09 |
| $95^{th}$ percentile | 169.37 | 17.86 | 246.30 | 21.20 | 1.97 | 1.29 |
| SD | 37.19 | 3.4 | 54.7 | 4.0 | 0.21 | 0.06 |
| % CV | 38 | 28 | 36 | 28 | 14 | 5 |

TABLE 6A-continued

Simulated and observed PK parameters and geometric mean $C_{max}$ and $AUC_{(0-\infty)}$ ratios for maribavir following a single oral dose of maribavir in the presence and absence of ketoconazole with associated variability in healthy adults.

| | Maribavir | | Maribavir + Ketoconazole | | Ratio | |
|---|---|---|---|---|---|---|
| | $AUC_{(0-\infty)}$ | $C_{max}$ | $AUC_{(0-\infty)}$ | $C_{max}$ | $AUC_{(0-\infty)}$ | $C_{max}$ |
| | mg/L*h | mg/L | mg/L*h | mg/L | | |
| OBSERVED | | | | | | |
| Mean | 126 | 19.8 | 194 | 21.8 | 1.55 | 1.12 |
| SD | 41.6 | 3.9 | 64.3 | 4.4 | 0.23 | 0.22 |
| % CV | 33 | 20 | 33 | 20 | 15 | 20 |
| Geometric mean | 119 | 19.4 | 183 | 21.3 | 1.53 | 1.10 |
| 90% CI around geometric mean (lower limit) | | | | | 1.44 | 1.01 |
| 90% CI around geometric mean (upper limit) | | | | | 1.63 | 1.19 |
| MEAN RATIO PREDICTED/OBSERVED | 0.79 | 0.62 | 0.78 | 0.66 | 0.99 | 1.05 |
| GEOMEAN RATIO PREDICTED/OBSERVED | 0.78 | 0.61 | 0.77 | 0.65 | 1.00 | 1.06 |

A comparison of observed and predicted plasma concentrations of maribavir following multiple oral doses of 400 mg administered in the absence of rifampicin and during concurrent treatment with rifampicin was performed. Subjects took maribavir 400 mg BID on Days 1-3 (5 doses), then rifampicin 600 mg QD on Days 4 through 12, followed by both maribavir 400 mg (BID) and rifampicin 600 mg QD on Days 13 and 14, with final doses of maribavir and rifampicin on the morning of Day 15. Associated geometric mean $C_{12h}$, $C_{max}$, and $AUC_{(0-12h)}$ values for maribavir in the presence or absence of rifampicin are shown in Table 7A. Predicted values for $C_{max}$ and AUC are within 1.25-fold of the observed parameter values.

TABLE 7A

Simulated and observed PK parameters and geometric mean $C_{max}$ and $AUC_{(0-12\,h)}$ ratios for maribavir following a single oral dose of maribavir in the presence and absence of rifampicin with associated variability in healthy adults.

| | Maribavir 400 mg BID | | | 400 mg BID Maribavir + 600 mg QD Rifampicin | | | Ratio | | |
|---|---|---|---|---|---|---|---|---|---|
| | $AUC_{(0-12\,h)}$ | $C_{max}$ | $C_{12\,h}$ | $AUC_{(0-12\,h)}$ | $C_{max}$ | $C_{12\,h}$ | $AUC_{(0-12\,h)}$ | $C_{max}$ | $C_{12\,h}$ |
| | mg/L*h | mg/L | mg/L | mg/L*h | mg/L | mg/L | | | |
| PREDICTED | | | | | | | | | |
| Mean | 95.28 | 14.26 | 2.88 | 35.13 | 7.97 | 0.340 | 0.37 | 0.56 | 0.09 |
| Median | 90.02 | 13.98 | 2.61 | 30.52 | 7.57 | 0.145 | 0.35 | 0.55 | 0.06 |
| Geometric Mean | 88.77 | 13.78 | 2.07 | 30.53 | 7.44 | 0.088 | 0.34 | 0.54 | 0.04 |
| 90% CI around geometric mean (lower limit) | 84.25 | 13.30 | 2.03 | 28.36 | 7.07 | 0.083 | 0.33 | 0.52 | 0.04 |
| 90% CI around geometric mean (upper limit) | 93.54 | 14.29 | 2.10 | 32.86 | 7.83 | 0.093 | 0.36 | 0.56 | 0.04 |
| 5th percentile | 41.15 | 8.76 | 0.39 | 12.44 | 3.95 | 0.002 | 0.17 | 0.33 | 0.01 |
| 95th percentile | 151.23 | 20.23 | 6.49 | 67.37 | 13.43 | 1.507 | 0.62 | 0.79 | 0.33 |
| SD | 35.28 | 3.7 | 2.1 | 18.64 | 2.93 | 0.53 | 0.14 | 0.14 | 0.11 |
| % CV | 37 | 26 | 73 | 53 | 37 | 151 | 37 | 25 | 112 |
| OBSERVED | | | | | | | | | |
| Mean | 89.9 | 16.9 | 2.54 | 35.1 | 10.2 | 0.41 | 0.41 | 0.65 | 0.17 |
| SD | 24.5 | 5.22 | 1.37 | 7.07 | 2.3 | 0.21 | 0.08 | 0.24 | 0.07 |
| % CV | 86.6 | 16.2 | 2.24 | 34.5 | 9.88 | 0.41 | 0.40 | 0.61 | 0.18 |
| RATIO MEAN PREDICTED/OBSERVED | 1.06 | 0.84 | 1.14 | 1.00 | 0.78 | 0.83 | 0.91 | 0.87 | 0.56 |
| RATIO GEOMETRIC MEAN PREDICTED/OBSERVED | 1.03 | 0.85 | 0.92 | 0.88 | 0.75 | 0.22 | 0.85 | 0.89 | 0.24 |

Model Verification
Simulation of Plasma Concentration-Time Profiles of Maribavir 800 mg BID in the Presence and Absence of 600 mg Rifampicin QD Predicted plasma concentration-time profiles of maribavir during 3 days of dosing (5 doses) at 800 mg BID in the absence and presence of 600 mg rifampicin once daily from day 1 to day 12 were generated. For each simulation, mean concentration-time profiles for each trial with 20 subjects, with a total virtual population of 200 subjects were used. The predicted PK parameters ($C_{max}$, $AUC_{(0-12h)}$ and $C_{12h}$) for the population are shown in Table 8A. The predicted PK parameters ($C_{max}$, $AUC_{(0-12h)}$ and $C_{12h}$) for this interaction is compared with the PK parameters for a 400 mg BID dose of maribavir in Table 9A.

Maribavir $C_{max}$ from 800 mg BID in the presence of 600 mg rifampicin QD was similar to that from maribavir 400 mg BID alone, however, $AUC_{(0-12)}$ was 23% lower and $C_{12h}$ was 75% lower. This indicates that increasing the maribavir dose from 400 mg BID to 800 mg BID cannot counteract the effect of rifampicin on the reduced therapeutic exposure to maribavir.

TABLE 8A

Predicted PK parameters for maribavir 800 mg BID in the presence and absence of rifampicin 600 mg QD.

| | Maribavir 800 mg BID | | | Maribavir 800 mg BID + 600 mg QD Rifampicin | | | Ratio | | |
|---|---|---|---|---|---|---|---|---|---|
| | $AUC_{(0-12\,h)}$ | $C_{max}$ | $C_{12\,h}$ | $AUC_{(0-12\,h)}$ | $C_{max}$ | $C_{12\,h}$ | $AUC_{(0-12\,h)}$ | $C_{max}$ | $C_{12\,h}$ |
| | mg/L* h | mg/L | mg/L | mg/L*h PREDICTED | mg/L | mg/L | | | |
| Mean | 194.99 | 28.96 | 5.95 | 73.25 | 16.40 | 0.73 | 0.37 | 0.56 | 0.10 |
| Median | 189.24 | 28.37 | 5.34 | 68.57 | 15.57 | 0.31 | 0.37 | 0.56 | 0.06 |
| Geometric Mean | 182.49 | 27.95 | 4.39 | 63.52 | 15.22 | 0.20 | 0.35 | 0.54 | 0.04 |
| 90% CI around geometric mean (lower limit) | 174.67 | 27.09 | 4.36 | 59.54 | 14.54 | 0.18 | 0.33 | 0.53 | 0.04 |
| 90% CI around geometric mean (upper limit) | 190.66 | 28.85 | 4.43 | 67.77 | 15.94 | 0.21 | 0.36 | 0.56 | 0.05 |
| 5th percentile | 94.23 | 17.97 | 0.93 | 24.65 | 7.93 | 0.00 | 0.18 | 0.35 | 0.00 |
| 95th percentile | 311.05 | 43.06 | 13.85 | 136.31 | 27.80 | 2.82 | 0.62 | 0.79 | 0.34 |
| SD | 68.94 | 7.68 | 4.00 | 38.65 | 6.25 | 1.09 | 0.14 | 0.14 | 0.11 |
| % CV | 35 | 26 | 67 | 53 | 38 | 149 | 37 | 25 | 108 |

TABLE 9A

Predicted PK parameters for maribavir 800 mg BID in the presence and absence of rifampicin 600 mg QD compared with PK parameters for maribavir 400 mg.

| | Maribavir 400 mg BID | | | Maribavir 800 mg BID + 600 mg QD Rifampicin | | | Ratio | | |
|---|---|---|---|---|---|---|---|---|---|
| | $AUC_{(0-12\,h)}$ | $C_{max}$ | $C_{12\,h}$ | $AUC_{(0-12\,h)}$ | $C_{max}$ | $C_{12\,h}$ | $AUC_{(0-12\,h)}$ | $C_{max}$ | $C_{12\,h}$ |
| | mg/L*h | mg/L | mg/L | mg/L*h PREDICTED | mg/L | mg/L | | | |
| Mean | 95.28 | 14.26 | 2.88 | 73.25 | 16.40 | 0.73 | 0.77 | 1.15 | 0.25 |
| Median | 90.02 | 13.98 | 2.61 | 68.57 | 15.57 | 0.31 | 0.76 | 1.11 | 0.12 |
| Geometric Mean | 88.77 | 13.78 | 2.07 | 63.52 | 15.22 | 0.20 | 0.72 | 1.10 | 0.10 |
| 90% CI around geometric mean (lower limit) | 84.25 | 13.3 | 2.03 | 59.54 | 14.54 | 0.18 | 0.71 | 1.09 | 0.09 |
| 90% CI around geometric mean (upper limit) | 93.54 | 14.29 | 2.1 | 67.77 | 15.94 | 0.21 | 0.72 | 1.12 | 0.10 |
| 5th percentile | 41.15 | 8.76 | 0.39 | 24.65 | 7.93 | 0.00 | 0.60 | 0.91 | 0.00 |
| 95th percentile | 151.23 | 20.34 | 6.49 | 136.31 | 27.80 | 2.82 | 0.90 | 1.37 | 0.43 |
| SD | 35.28 | 3.7 | 2.1 | 38.65 | 6.25 | 1.09 | 1.10 | 1.69 | 0.52 |
| % CV | 37 | 26 | 73 | 53 | 38 | 149 | 1.43 | 1.46 | 2.04 |

Simulation of Plasma Concentration-Time Profiles of Maribavir 1200 mg BID in the Presence and Absence of 600 mg Rifampicin QD Predicted plasma concentration-time profiles of maribavir during 3 days of dosing (5 doses) at 1200 mg BID in the absence and presence of 600 mg rifampicin once daily from day 1 to day 12 were generated. For each simulation, mean concentration-time profiles for each trial with 20 subjects, with a total virtual population of 200 subjects were used. The predicted PK parameters ($C_{max}$, $AUC_{(0-12h)}$ and $C_{12h}$) for the population are shown in Table 10A. Predicted PK parameters for maribavir 1200 mg BID in the presence of rifampicin 600 mg QD compared with PK parameters for maribavir 400 mg BID are presented in Table 11A.

Maribavir AUC from 1200 mg BID in the presence of 600 mg rifampicin QD was similar to that from maribavir 400 mg BID alone while the $C_{max}$ was slightly higher. However, the geometric mean $C_{12h}$ was 86% lower, indicating that increasing maribavir dose from 400 mg BID to 1200 mg BID cannot counteract the effect of rifampicin from an efficacy perspective (mainly driven by $C_{12h}$). Increasing the maribavir dose to 1600 mg BID had a minimal effect on the geometric mean $C_{12h}$, which was 81% lower than that with a 400 mg BID dose of maribavir.

TABLE 10A

Predicted PK parameters for maribavir 1200 mg BID in the presence and absence of rifampicin 600 mg QD.

| | Maribavir 1200 mg BID | | | Maribavir 1200 mg BID + 600 mg QD Rifampicin | | | Ratio | | |
|---|---|---|---|---|---|---|---|---|---|
| | $AUC_{(0-12\,h)}$ | $C_{max}$ | $C_{12\,h}$ | $AUC_{(0-12\,h)}$ | $C_{max}$ | $C_{12\,h}$ | $AUC_{(0-12\,h)}$ | $C_{max}$ | $C_{12\,h}$ |
| | mg/L*h | mg/L | mg/L | mg/L*h PREDICTED | mg/L | mg/L | | | |
| Mean | 292.48 | 43.44 | 8.93 | 109.87 | 24.59 | 1.10 | 0.37 | 0.56 | 0.10 |
| Median | 283.87 | 42.55 | 8.00 | 102.85 | 23.35 | 0.47 | 0.37 | 0.56 | 0.06 |
| Geometric Mean | 273.73 | 41.93 | 6.59 | 95.28 | 22.84 | 0.30 | 0.35 | 0.54 | 0.04 |
| 90% CI around geometric mean (lower limit) | 262.00 | 40.63 | 6.55 | 89.31 | 21.81 | 0.28 | 0.33 | 0.53 | 0.04 |
| 90% CI around geometric mean (upper limit) | 285.99 | 43.27 | 6.62 | 101.65 | 23.91 | 0.31 | 0.36 | 0.56 | 0.05 |
| 5th percentile | 141.35 | 26.96 | 1.40 | 36.97 | 11.90 | 0.00 | 0.18 | 0.35 | 0.00 |
| 95th percentile | 466.58 | 64.59 | 20.77 | 204.46 | 41.71 | 4.23 | 0.62 | 0.79 | 0.34 |
| SD | 108.42 | 11.45 | 6.00 | 57.57 | 9.37 | 1.63 | 0.14 | 0.14 | 0.11 |
| % CV | 35 | 26 | 67 | 53 | 38 | 149 | 37 | 25 | 108 |

TABLE 11A

Predicted PK parameters for maribavir 1200 mg BID in the presence of rifampicin 600 mg QD compared with PK parameters for maribavir 400 mg BID.

| | Maribavir 400 mg BID | | | Maribavir 1200 mg BID + 600 mg QD Rifampicin | | | Ratio | | |
|---|---|---|---|---|---|---|---|---|---|
| | $AUC_{(0-12\,h)}$ | $C_{max}$ | $C_{12\,h}$ | $AUC_{(0-12\,h)}$ | $C_{max}$ | $C_{12\,h}$ | $AUC_{(0-12\,h)}$ | $C_{max}$ | $C_{12\,h}$ |
| | mg/L*h | mg/L | mg/L | mg/L*h PREDICTED | mg/L | mg/L | | | |
| Mean | 95.28 | 14.26 | 2.89 | 109.87 | 24.59 | 1.10 | 1.15 | 1.72 | 0.38 |
| Median | 90.02 | 13.98 | 2.61 | 102.85 | 23.35 | 0.47 | 1.14 | 1.67 | 0.18 |
| Geometric Mean | 88.77 | 13.78 | 2.07 | 95.28 | 22.84 | 0.30 | 1.07 | 1.66 | 0.14 |
| 90% CI around geometric mean (lower limit) | 84.25 | 13.3 | 2.03 | 89.31 | 21.81 | 0.28 | 1.06 | 1.64 | 0.14 |
| 90% CI around geometric mean (upper limit) | 93.54 | 14.29 | 2.1 | 101.65 | 23.91 | 0.31 | 1.09 | 1.67 | 0.15 |
| 5th percentile | 41.15 | 8.76 | 0.39 | 36.97 | 11.90 | 0.00 | 0.90 | 1.36 | 0.00 |
| 95th percentile | 151.23 | 20.34 | 6.49 | 204.46 | 41.71 | 4.23 | 1.35 | 2.05 | 0.65 |
| SD | 35.28 | 3.7 | 2.1 | 57.57 | 9.37 | 1.63 | 1.63 | 2.53 | 0.78 |
| % CV | 37 | 26 | 73 | 53 | 38 | 149 | 1.43 | 1.46 | 2.04 |

Simulation of Plasma Concentration-Time Profiles of Maribavir 400 mg BID in the Presence and Absence of 100 mg Phenobarbital QD Predicted plasma concentration-time profiles of maribavir during 3 days of dosing (5 doses) at 400 mg BID in the absence and presence of 100 mg phenobarbital once daily from day 1 to day 12 were generated. For each simulation, mean concentration-time profiles for each trial with 20 subjects, with a total virtual population of 200 subjects were used. The predicted PK parameters ($C_{max}$, $AUC_{(0-12h)}$ and $C_{12h}$) for the population are shown in Table 12A. Induction of CYP3A4 by phenobarbital resulted in a mean decrease of 39%, 27% and 63% in $AUC_{(0-12h)}$, $C_{max}$ and $C_{12h}$, respectively.

TABLE 12A

Predicted PK parameters for maribavir 400 mg BID in the presence and absence of phenobarbital 100 mg QD.

| | Maribavir 400 mg BID | | | Maribavir 400 mg BID + 100 mg QD Phenobarbital | | | Ratio | | |
|---|---|---|---|---|---|---|---|---|---|
| | $AUC_{(0-12\ h)}$ | $C_{max}$ | $C_{12\ h}$ | $AUC_{(0-12\ h)}$ | $C_{max}$ | $C_{12\ h}$ | | | |
| | mg/L*h | mg/L | mg/L | mg/L*h PREDICTED | mg/L | mg/L | $AUC_{(0-12\ h)}$ | $C_{max}$ | $C_{12\ h}$ |
| Mean | 99.72 | 14.66 | 3.12 | 61.20 | 10.66 | 1.33 | 0.61 | 0.73 | 0.37 |
| Median | 93.26 | 14.23 | 2.40 | 55.41 | 10.44 | 0.85 | 0.63 | 0.75 | 0.37 |
| Geometric Mean | 92.65 | 14.09 | 2.29 | 55.66 | 10.21 | 0.72 | 0.60 | 0.72 | 0.31 |
| 90% CI around geometric mean (lower limit) | 88.54 | 13.63 | 2.27 | 52.88 | 9.86 | 0.70 | 0.59 | 0.71 | 0.31 |
| 90% CI around geometric mean (upper limit) | 96.96 | 14.57 | 2.31 | 58.60 | 10.57 | 0.73 | 0.62 | 0.74 | 0.31 |
| 5th percentile | 47.52 | 9.12 | 0.50 | 27.75 | 6.18 | 0.07 | 0.39 | 0.56 | 0.07 |
| 95th percentile | 169.70 | 21.94 | 7.30 | 112.27 | 16.47 | 4.17 | 0.78 | 0.86 | 0.65 |
| SD | 38.6 | 4.1 | 2.26 | 26.96 | 3.12 | 1.25 | 0.12 | 0.09 | 0.18 |
| % CV | 38 | 28 | 72 | 44 | 29 | 101 | 20 | 13 | 47 |

Simulation of Plasma Concentration-Time Profiles of Maribavir 800 mg BID in the Presence and Absence of 100 mg Phenobarbital QD Predicted plasma concentration-time profiles of maribavir during 3 days of dosing (5 doses) at 800 mg BID in the absence and presence of 100 mg phenobarbital once daily from day 1 to day 12 were generated. For each simulation, mean concentration-time profiles for each trial with 10 subjects, with a total virtual population of 200 subjects were used. The predicted PK parameters ($C_{max}$, $AUC_{(0-12h)}$ and $C_{12h}$ for the population are shown in Table 13A. Predicted PK parameters for maribavir 800 mg BID in the presence of phenobarbital 100 mg QD compared with PK parameters for maribavir 400 mg BID are presented in Table 14A.

Maribavir AUC and $C_{max}$ from 800 mg BID in the presence of 100 mg phenobarbital QD were marginally lower than those from maribavir 800 mg BID alone. However, $C_{min}$ was 63% lower than with maribavir 800 mg alone. Increasing the maribavir dose given with phenobarbital from 400 mg BID to 800 mg BID results in a mean $C_{min}$ that is 15% lower than that with 400 mg BID maribavir alone. Thus, by increasing the dose of maribavir to 800 mg BID, the interaction is counteracted significantly.

TABLE 13A

Predicted PK parameters for maribavir 800 mg BID in the presence and absence of phenobarbital 100 mg QD.

| | Maribavir 800 mg BID | | | Maribavir 800 mg BID + 100 mg QD Phenobarbital | | | Ratio | | |
|---|---|---|---|---|---|---|---|---|---|
| | $AUC_{(0-12\ h)}$ | $C_{max}$ | $C_{12\ h}$ | $AUC_{(0-12\ h)}$ | $C_{max}$ | $C_{12\ h}$ | | | |
| | mg/L*h | mg/L | mg/L | mg/L*h PREDICTED | mg/L | mg/L | $AUC_{(0-12\ h)}$ | $C_{max}$ | $C_{12\ h}$ |
| Mean | 199.43 | 29.32 | 6.24 | 122.40 | 21.32 | 2.66 | 0.61 | 0.73 | 0.37 |
| Median | 186.51 | 28.46 | 4.81 | 110.83 | 20.88 | 1.70 | 0.63 | 0.75 | 0.37 |
| Geometric Mean | 185.31 | 28.19 | 4.58 | 111.33 | 20.42 | 1.43 | 0.60 | 0.72 | 0.31 |
| 90% CI around geometric mean (lower limit) | 177.07 | 27.26 | 4.54 | 105.75 | 19.72 | 1.41 | 0.59 | 0.71 | 0.31 |

TABLE 13A-continued

Predicted PK parameters for maribavir 800 mg BID in
the presence and absence of phenobarbital 100 mg QD.

| | Maribavir 800 mg BID | | | Maribavir 800 mg BID + 100 mg QD Phenobarbital | | | Ratio | | |
|---|---|---|---|---|---|---|---|---|---|
| | $AUC_{(0-12\,h)}$ | $C_{max}$ | $C_{12\,h}$ | $AUC_{(0-12\,h)}$ | $C_{max}$ | $C_{12\,h}$ | $AUC_{(0-12\,h)}$ | $C_{max}$ | $C_{12\,h}$ |
| | mg/L*h | mg/L | mg/L | mg/L*h PREDICTED | mg/L | mg/L | | | |
| 90% CI around geometric mean (upper limit) | 193.93 | 29.14 | 4.62 | 117.20 | 21.14 | 1.45 | 0.62 | 0.74 | 0.31 |
| 5th percentile | 95.04 | 18.24 | 1.00 | 55.49 | 12.35 | 0.14 | 0.39 | 0.56 | 0.07 |
| 95th percentile | 339.40 | 43.89 | 14.60 | 224.54 | 32.93 | 8.33 | 0.78 | 0.86 | 0.65 |
| SD | 36.3 | 8.2 | 4.53 | 53.9 | 6.24 | 2.7 | 0.12 | 0.09 | 0.18 |
| % CV | 38 | 28 | 73 | 44 | 29 | 101 | 20 | 13 | 48 |

TABLE 14A

Predicted PK parameters for maribavir 800 mg BID in the presence of phenobarbital
100 mg QD compared with PK parameters for maribavir 400 mg BID.

| | Maribavir 400 mg BID | | | Maribavir 800 mg BID + 100 mg QD Phenobarbital | | | Ratio | | |
|---|---|---|---|---|---|---|---|---|---|
| | $AUC_{(0-12\,h)}$ | $C_{max}$ | $C_{12\,h}$ | $AUC_{(0-12\,h)}$ | $C_{max}$ | $C_{12\,h}$ | $AUC_{(0-12\,h)}$ | $C_{max}$ | $C_{12\,h}$ |
| | mg/L*h | mg/L | mg/L | mg/L*h PREDICTED | mg/L | mg/L | | | |
| Mean | 99.72 | 14.66 | 3.12 | 122.40 | 21.32 | 2.66 | 1.23 | 1.45 | 0.85 |
| Median | 93.26 | 14.23 | 2.40 | 110.83 | 20.88 | 1.70 | 1.19 | 1.47 | 0.71 |
| Geometric Mean | 92.65 | 14.09 | 2.29 | 111.33 | 20.42 | 1.43 | 1.20 | 1.45 | 0.62 |
| 90% CI around geometric mean (lower limit) | 88.54 | 13.63 | 2.27 | 105.75 | 19.72 | 1.41 | 1.19 | 1.45 | 0.62 |
| 90% CI around geometric mean (upper limit) | 96.96 | 14.57 | 2.31 | 117.20 | 21.14 | 1.45 | 1.21 | 1.45 | 0.63 |
| 5th percentile | 47.52 | 9.12 | 0.50 | 55.49 | 12.35 | 0.14 | 1.17 | 1.35 | 0.28 |
| 95th percentile | 169.70 | 21.94 | 7.30 | 224.54 | 32.93 | 8.33 | 1.32 | 1.50 | 1.14 |
| SD | 38.6 | 4.1 | 2.26 | 53.9 | 6.24 | 2.7 | 1.40 | 1.52 | 1.19 |
| % CV | 38 | 28 | 72 | 44 | 29 | 101 | 1.16 | 1.04 | 1.40 |

Simulation of Plasma Concentration-Time Profiles of Maribavir 1200 mg BID in the Presence and Absence of 100 mg Phenobarbital QD Predicted plasma concentration-time profiles of maribavir during 3 days of dosing (5 doses) at 1200 mg BID in the absence and presence of 100 mg phenobarbital once daily from day 1 to day 12 were generated. For each simulation, mean concentration-time profiles for each trial with 10 subjects, with a total virtual population of 200 subjects were used. The predicted PK parameters ($C_{max}$, $AUC_{(0-12h)}$ and $C_{12h}$) for the population are shown in Table 15A. Predicted PK parameters for maribavir 1200 mg BID in the presence of phenobarbital 100 mg QD compared with PK parameters for maribavir 400 mg BID are presented in Table 16A.

Maribavir AUC and $C_{max}$ from 1200 mg BID in the presence of 100 mg phenobarbital QD were about 2 times higher those from maribavir 400 mg BID alone while $C_{min}$ is about 28% higher. Increasing the maribavir dose from 400 mg BID to 1200 mg BID can counteract the effect of phenobarbital. If the higher exposure (as seen with AUC and Cmax) is not detrimental to treatment, it can be concluded that the maribavir dose should be adjusted from 400 mg BID to 1200 mg BID when co-administration with phenobarbital is needed.

TABLE 15A

Predicted PK parameters for maribavir 1200 mg BID in the presence and absence of phenobarbital 100 mg QD.

| | Maribavir 1200 mg BID | | | Maribavir 1200 mg BID + 100 mg QD Phenobarbital | | | Ratio | | |
|---|---|---|---|---|---|---|---|---|---|
| | $AUC_{(0-12\,h)}$ | $C_{max}$ | $C_{12\,h}$ | $AUC_{(0-12\,h)}$ | $C_{max}$ | $C_{12\,h}$ | $AUC_{(0-12\,h)}$ | $C_{max}$ | $C_{12\,h}$ |
| | mg/L*h | mg/L | mg/L | mg/L*h PREDICTED | mg/L | mg/L | | | |
| Mean | 299.15 | 43.98 | 9.36 | 183.60 | 31.98 | 3.99 | 0.61 | 0.73 | 0.37 |
| Median | 279.77 | 42.69 | 7.21 | 166.24 | 31.31 | 2.55 | 0.63 | 0.75 | 0.37 |
| Geometric Mean | 277.96 | 42.28 | 6.88 | 166.99 | 30.63 | 2.15 | 0.60 | 0.72 | 0.31 |
| 90% CI around geometric mean (lower limit) | 265.61 | 40.90 | 6.82 | 158.62 | 29.58 | 2.11 | 0.59 | 0.71 | 0.31 |
| 90% CI around geometric mean (upper limit) | 290.89 | 43.71 | 6.94 | 175.80 | 31.71 | 2.18 | 0.62 | 0.74 | 0.31 |
| 5$^{th}$ percentile | 142.56 | 27.35 | 1.50 | 83.24 | 18.53 | 0.21 | 0.39 | 0.56 | 0.07 |
| 95$^{th}$ percentile | 509.10 | 65.83 | 21.89 | 336.81 | 49.40 | 12.50 | 0.78 | 0.86 | 0.65 |
| SD | 114.5 | 12.3 | 6.8 | 80.9 | 9.36 | 4.04 | 0.12 | 0.09 | 0.18 |
| % CV | 38 | 28 | 73 | 44 | 29 | 101 | 20 | 13 | 47.97 |

TABLE 16A

Predicted PK parameters for marvibavir 1200 mg BID in the presence of phenobarbital 100 mg QD compared with PK parameters for maribavir 400 mg BID.

| | Maribavir 400 mg BID | | | Maribavir 1200 mg BID + 100 mg QD Phenobarbital | | | Ratio | | |
|---|---|---|---|---|---|---|---|---|---|
| | $AUC_{(0-12\,h)}$ | $C_{max}$ | $C_{12\,h}$ | $AUC_{(0-12\,h)}$ | $C_{max}$ | $C_{12\,h}$ | $AUC_{(0-12\,h)}$ | $C_{max}$ | $C_{12\,h}$ |
| | mg/L*h | mg/L | mg/L | mg/L*h PREDICTED | mg/L | mg/L | | | |
| Mean | 99.72 | 14.66 | 3.12 | 183.60 | 31.98 | 3.99 | 1.84 | 2.18 | 1.28 |
| Median | 93.26 | 14.23 | 2.40 | 166.24 | 31.31 | 2.55 | 1.78 | 2.20 | 1.06 |
| Geometric Mean | 92.65 | 14.09 | 2.29 | 166.99 | 30.63 | 2.15 | 1.80 | 2.17 | 0.94 |
| 90% CI around geometric mean (lower limit) | 88.54 | 13.63 | 2.27 | 158.62 | 29.58 | 2.11 | 1.79 | 2.17 | 0.93 |
| 90% CI around geometric mean (upper limit) | 96.96 | 14.57 | 2.31 | 175.80 | 31.71 | 2.18 | 1.81 | 2.18 | 0.94 |
| 5$^{th}$ percentile | 47.52 | 9.12 | 0.50 | 83.24 | 18.53 | 0.21 | 1.75 | 2.03 | 0.42 |
| 95$^{th}$ percentile | 169.70 | 21.94 | 7.30 | 336.81 | 49.40 | 12.50 | 1.98 | 2.25 | 1.71 |
| SD | 38.6 | 4.1 | 2.26 | 80.9 | 9.36 | 4.04 | 2.10 | 2.28 | 1.79 |
| % CV | 38 | 28 | 72 | 44 | 29 | 101 | 1.16 | 1.04 | 1.40 |

Simulation of Plasma Concentration-Time Profiles of Maribavir 400 mg BID in the Presence and Absence of 300 mg Phenytoin QD Predicted plasma concentration-time profiles of maribavir during 3 days of dosing (5 doses) at 400 mg BID in the absence and presence of 300 mg phenytoin once daily from day 1 to day 12 were generated. For each simulation, mean concentration-time profiles for each trial with 10 subjects, with a total virtual population of 200 subjects were used. The predicted PK parameters ($C_{max}$, $AUC_{(0-12h)}$ and $C_{12h}$) for the population are shown in Table 17A.

Induction of CYP3A4 by phenobarbital resulted in a mean decrease of 42%, 31% and 64% in $AUC_{(0-12)}$, $C_{max}$ and $C_{12h}$, respectively.

TABLE 17A

Predicted PK parameters for maribavir 400 mg BID in the presence and absence of phenytoin 300 mg QD.

| | Maribavir 400 mg BID | | | Maribavir 400 mg BID + 300 mg QD Phenytoin | | | Ratio | | |
|---|---|---|---|---|---|---|---|---|---|
| | $AUC_{(0-12\ h)}$ | $C_{max}$ | $C_{12\ h}$ | $AUC_{(0-12\ h)}$ | $C_{max}$ | $C_{12\ h}$ | $AUC_{(0-12\ h)}$ | $C_{max}$ | $C_{12\ h}$ |
| | mg/L*h | mg/L | mg/L | mg/L*h PREDICTED | mg/L | mg/L | | | |
| Mean | 99.72 | 14.66 | 3.12 | 56.81 | 10.04 | 1.16 | 0.58 | 0.69 | 0.36 |
| Median | 93.26 | 14.23 | 2.40 | 56.31 | 9.95 | 0.81 | 0.58 | 0.69 | 0.35 |
| Geometric Mean | 92.65 | 14.09 | 2.29 | 52.42 | 9.63 | 0.68 | 0.57 | 0.68 | 0.30 |
| 90% CI around geometric mean (lower limit) | 88.54 | 13.63 | 2.27 | 49.99 | 9.30 | 0.67 | 0.55 | 0.67 | 0.30 |
| 90% CI around geometric mean (upper limit) | 96.96 | 14.57 | 2.31 | 54.98 | 9.96 | 0.69 | 0.58 | 0.70 | 0.30 |
| 5$^{th}$ percentile | 47.52 | 9.12 | 0.50 | 26.75 | 5.59 | 0.09 | 0.35 | 0.50 | 0.09 |
| 95$^{th}$ percentile | 169.70 | 21.94 | 7.30 | 99.79 | 14.78 | 3.33 | 0.82 | 0.88 | 0.68 |
| SD | 38.6 | 4.1 | 2.26 | 23.0 | 2.91 | 1.1 | 0.14 | 0.11 | 0.18 |
| % CV | 38 | 28 | 72 | 40 | 29 | 95 | 24 | 17 | 51.07 |

Simulation of Plasma Concertation-Time Profiles of Maribavir 800 mg BID in the Presence and Absence of 300 mg Phenytoin QD Predicted plasma concentration-time profiles of maribavir during 3 days of dosing (5 doses) at 800 mg BID in the absence and presence of 300 mg phenytoin once daily from day 1 to day 12 were generated. For each simulation, mean concentration-time profiles for each trial with 10 subjects, with a total virtual population of 200 subjects were used. The predicted PK parameters ($C_{max}$, $AUC_{(0-12h)}$ and $C_{12h}$) for the population are shown in Table 18A. Predicted PK parameters for maribavir 800 mg BID in the presence of phenytoin 300 mg QD compared with PK parameters for maribavir 400 mg BID are presented in Table 19A.

Maribavir AUC and Cmax from 800 mg BID in the presence of 300 mg phenytoin QD was marginally higher than those from maribavir 400 mg BID alone, however, $C_{min}$ was 26% lower. Increasing the maribavir dose from 400 mg BID to 800 mg BID cannot counteract the effect of phenytoin from an efficacy perspective (mainly driven by $C_{min}$).

TABLE 18A

Predicted PK parameters for maribavir 800 mg BID in the presence and absence of phenytoin 300 mg QD.

| | Maribavir 800 mg BID | | | Maribavir 800 mg BID + 300 mg QD Phenytoin | | | Ratio | | |
|---|---|---|---|---|---|---|---|---|---|
| | $AUC_{(0-12\ h)}$ | $C_{max}$ | $C_{12\ h}$ | $AUC_{(0-12\ h)}$ | $C_{max}$ | $C_{12\ h}$ | $AUC_{(0-12\ h)}$ | $C_{max}$ | $C_{12\ h}$ |
| | mg/L*h | mg/L | mg/L | mg/L*h PREDICTED | mg/L | mg/L | | | |
| Mean | 199.43 | 29.32 | 6.24 | 113.63 | 20.08 | 2.32 | 0.58 | 0.69 | 0.36 |
| Median | 186.51 | 28.46 | 4.81 | 112.62 | 19.90 | 1.62 | 0.58 | 0.69 | 0.35 |
| Geometric Mean | 185.31 | 28.19 | 4.58 | 104.85 | 19.26 | 1.36 | 0.57 | 0.68 | 0.30 |
| 90% CI around geometric mean (lower limit) | 177.07 | 27.26 | 4.54 | 99.97 | 18.61 | 1.34 | 0.55 | 0.67 | 0.30 |

TABLE 18A-continued

Predicted PK parameters for maribavir 800 mg BID in the presence and absence of phenytoin 300 mg QD.

|  | Maribavir 800 mg BID | | | Maribavir 800 mg BID + 300 mg QD Phenytoin | | | Ratio | | |
| --- | --- | --- | --- | --- | --- | --- | --- | --- | --- |
|  | $AUC_{(0-12\,h)}$ | $C_{max}$ | $C_{12\,h}$ | $AUC_{(0-12\,h)}$ | $C_{max}$ | $C_{12\,h}$ | $AUC_{(0-12\,h)}$ | $C_{max}$ | $C_{12\,h}$ |
|  | mg/L*h | mg/L | mg/L | mg/L*h PREDICTED | mg/L | mg/L |  |  |  |
| 90% CI around geometric mean (upper limit) | 193.93 | 29.14 | 4.62 | 109.96 | 19.93 | 1.38 | 0.58 | 0.70 | 0.30 |
| 5th percentile | 95.04 | 18.24 | 1.00 | 53.51 | 11.18 | 0.18 | 0.35 | 0.50 | 0.09 |
| 95th percentile | 339.40 | 43.89 | 14.60 | 199.59 | 29.57 | 6.65 | 0.82 | 0.88 | 0.68 |
| SD | 76.33 | 8.2 | 4.53 | 46.1 | 5.83 | 2.2 | 0.14 | 0.11 | 0.18 |
| % CV | 38 | 28 | 73 | 40 | 29 | 95 | 24 | 17 | 51 |

TABLE 19A

Predicted PK parameters for maribavir 800 mg BID in the presence of phenytoin 300 mg QD compared with PK parameters for maribavir 400 mg BID.

|  | Maribavir 400 mg BID | | | Maribavir 800 mg BID + 300 mg QD Phenytoin | | | Ratio | | |
| --- | --- | --- | --- | --- | --- | --- | --- | --- | --- |
|  | $AUC_{(0-12\,h)}$ | $C_{max}$ | $C_{12\,h}$ | $AUC_{(0-12\,h)}$ | $C_{max}$ | $C_{12\,h}$ | $AUC_{(0-12\,h)}$ | $C_{max}$ | $C_{12\,h}$ |
|  | mg/L*h | mg/L | mg/L | mg/L*h PREDICTED | mg/L | mg/L |  |  |  |
| Mean | 99.72 | 14.66 | 3.12 | 113.63 | 20.08 | 2.32 | 1.14 | 1.37 | 0.74 |
| Median | 93.26 | 14.23 | 2.40 | 112.62 | 19.90 | 1.62 | 1.21 | 1.40 | 0.68 |
| Geometric Mean | 92.65 | 14.09 | 2.29 | 104.85 | 19.26 | 1.36 | 1.13 | 1.37 | 0.59 |
| 90% CI around geometric mean (lower limit) | 88.54 | 13.63 | 2.27 | 99.97 | 18.61 | 1.34 | 1.13 | 1.37 | 0.59 |
| 90% CI around geometric mean (upper limit) | 96.96 | 14.57 | 2.31 | 109.96 | 19.93 | 1.38 | 1.13 | 1.37 | 0.60 |
| 5th percentile | 47.52 | 9.12 | 0.50 | 53.51 | 11.18 | 0.18 | 1.13 | 1.23 | 0.36 |
| 95th percentile | 169.70 | 21.94 | 7.30 | 199.59 | 29.57 | 6.65 | 1.18 | 1.35 | 0.91 |
| SD | 38.6 | 4.1 | 2.26 | 46.1 | 5.83 | 2.2 | 1.21 | 1.42 | 0.97 |
| % CV | 38 | 28 | 72 | 40 | 29 | 95 | 1.05 | 1.04 | 1.30 |

Simulation of Plasma Concentration-Time Profiles of Maribavir 1200 mg BID in the Presence and Absence of 300 mg Phenytoin QD Predicted plasma concentration-time profiles of maribavir during 3 days of dosing (5 doses) at 1200 mg BID in the absence and presence of 300 mg phenytoin once daily from day 1 to day 12 were generated. For each simulation, mean concentration-time profiles for each trial with 10 subjects, with a total virtual population of 200 subjects were used. The predicted PK parameters ($C_{max}$, $AUC_{(0-24h)}$ and $C_{12h}$) for the population are shown in Table 20A. Predicted PK parameters for maribavir 1200 mg BID in the presence of phenytoin 300 mg QD compared with PK parameters for maribavir 400 mg BID are presented in Table 21A.

Maribavir AUC and $C_{max}$ from 1200 mg BID in the presence of 300 mg phenytoin QD were about 2-fold higher than those from maribavir 400 mg BID alone, but $C_{min}$ was similar to that of 400 mg maribavir alone, suggesting that increasing the maribavir dose from 400 mg BID to 1200 mg BID can counteract the effect of phenytoin from an efficacy perspective (mainly driven by $C_{min}$). The impact of the higher exposure (AUC and $C_{max}$) will have to be evaluated.

TABLE 20A

Predicted PK parameters for maribavir 1200 mg BID in the presence and absence of phenytoin 300 mg QD.

| | Maribavir 1200 mg BID | | | Maribavir 1200 mg BID + 300 mg QD Phenytoin | | | Ratio | | |
|---|---|---|---|---|---|---|---|---|---|
| | $AUC_{(0-12\,h)}$ | $C_{max}$ | $C_{12\,h}$ | $AUC_{(0-12\,h)}$ | $C_{max}$ | $C_{12\,h}$ | $AUC_{(0-12\,h)}$ | $C_{max}$ | $C_{12\,h}$ |
| | mg/L*h | mg/L | mg/L | mg/L*h PREDICTED | mg/L | mg/L | | | |
| Mean | 299.15 | 43.98 | 9.36 | 170.44 | 30.13 | 3.48 | 0.58 | 0.69 | 0.36 |
| Median | 279.77 | 42.69 | 7.21 | 168.93 | 29.85 | 2.42 | 0.58 | 0.69 | 0.35 |
| Geometric Mean | 277.96 | 42.28 | 6.88 | 157.27 | 28.88 | 2.05 | 0.57 | 0.68 | 0.30 |
| 90% CI around geometric mean (lower limit) | 265.61 | 40.90 | 6.82 | 149.96 | 27.91 | 2.02 | 0.55 | 0.67 | 0.30 |
| 90% CI around geometric mean (upper limit) | 290.89 | 43.71 | 6.94 | 164.94 | 29.89 | 2.08 | 0.58 | 0.70 | 0.30 |
| 5th percentile | 142.56 | 27.35 | 1.50 | 80.26 | 16.76 | 0.27 | 0.35 | 0.50 | 0.09 |
| 95th percentile | 509.10 | 65.83 | 21.89 | 299.38 | 44.35 | 9.98 | 0.82 | 0.88 | 0.68 |
| SD | 114.5 | 12.3 | 6.8 | 69.01 | 8.7 | 3.29 | 0.14 | 0.11 | 0.18 |
| % CV | 38 | 28 | 73 | 40 | 29 | 95 | 24 | 17 | 52 |

TABLE 21A

Predicted PK parameters for maribavir 1200 mg BID in the presence of phenytoin 300 mg QD compared with PK parameters for maribavir 400 mg BID.

| | Maribavir 400 mg BID | | | Maribavir 1200 mg BID + 300 mg QD Phenytoin | | | Ratio | | |
|---|---|---|---|---|---|---|---|---|---|
| | $AUC_{(0-12\,h)}$ | $C_{max}$ | $C_{12\,h}$ | $AUC_{(0-12\,h)}$ | $C_{max}$ | $C_{12\,h}$ | $AUC_{(0-12\,h)}$ | $C_{max}$ | $C_{12\,h}$ |
| | mg/L*h | mg/L | mg/L | mg/L*h PREDICTED | mg/L | mg/L | | | |
| Mean | 99.72 | 14.66 | 3.12 | 170.44 | 30.13 | 3.48 | 1.71 | 2.06 | 1.12 |
| Median | 93.26 | 14.23 | 2.40 | 168.93 | 29.85 | 2.42 | 1.81 | 2.10 | 1.01 |
| Geometric Mean | 92.65 | 14.09 | 2.29 | 157.27 | 28.88 | 2.05 | 1.70 | 2.05 | 0.90 |
| 90% CI around geometric mean (lower limit) | 88.54 | 13.63 | 2.27 | 149.96 | 27.91 | 2.02 | 1.69 | 2.05 | 0.89 |
| 90% CI around geometric mean (upper limit) | 96.96 | 14.57 | 2.31 | 164.94 | 29.89 | 2.08 | 1.70 | 2.05 | 0.90 |
| 5th percentile | 47.52 | 9.12 | 0.50 | 80.26 | 16.76 | 0.27 | 1.69 | 1.84 | 0.54 |
| 95th percentile | 169.70 | 21.94 | 7.30 | 299.38 | 44.35 | 9.98 | 1.76 | 2.02 | 1.37 |
| SD | 38.2 | 4.1 | 2.26 | 69.01 | 8.7 | 3.29 | 1.81 | 2.12 | 1.46 |
| % CV | 38 | 28 | 72 | 40 | 29 | 95 | 1.05 | 1.04 | 1.30 |

Simulation of Plasma Concentration-Time Profiles for Maribavir 400 mg BID in the Presence and Absence of Carbamazepine Predicted plasma concentration-time profiles of maribavir during 3 days of dosing (5 doses, starting on day 15) at 400 mg BID in the absence and presence of once daily carbamazepine QD (200 mg on day 1 and 2, and 400 mg on day 3 to day 17) were generated. For each simulation, mean concentration-time profiles for each trial with 10 subjects, with a total virtual population of 200 subjects were used. The predicted PK parameters ($C_{max}$, $AUC_{(0-12h)}$ and $C_{12h}$) for the population are shown in Table 22A.

Due to CYP3A4 induction by carbamazepine, a mean decrease of 46% in maribavir $C_{12h}$ (efficacy marker) and a 29% and 23% decrease in AUC and $C_{max}$ respectively, is predicted when 400 mg BID maribavir is combined with carbamazepine.

TABLE 22A

Predicted PK parameters for maribavir 400 mg BID in the presence and absence of carbamazepine.

| | Maribavir 400 mg BID | | | Maribavir 400 mg BID + 400 mg QD carbazepine | | | Ratio | | |
|---|---|---|---|---|---|---|---|---|---|
| | $AUC_{(0-12\,h)}$ | $C_{max}$ | $C_{12\,h}$ | $AUC_{(0-12\,h)}$ | $C_{max}$ | $C_{12\,h}$ | $AUC_{(0-12\,h)}$ | $C_{max}$ | $C_{12\,h}$ |
| | mg/L*h | mg/L | mg/L | mg/L*h PREDICTED | mg/L | mg/L | | | |
| Mean | 98.93 | 14.60 | 3.11 | 67.85 | 11.12 | 1.65 | 0.71 | 0.77 | 0.54 |
| Median | 88.34 | 13.91 | 2.34 | 63.37 | 10.80 | 1.29 | 0.71 | 0.79 | 0.56 |
| Geometric Mean | 91.25 | 14.01 | 2.18 | 63.82 | 10.74 | 1.15 | 0.70 | 0.77 | 0.53 |
| 90% CI around geometric mean (lower limit) | 87.05 | 13.54 | 2.16 | 61.25 | 10.41 | 1.14 | 0.69 | 0.76 | 0.53 |
| 90% CI around geometric mean (upper limit) | 95.66 | 14.49 | 2.21 | 66.49 | 11.08 | 1.16 | 0.71 | 0.78 | 0.53 |
| 5th percentile | 48.05 | 8.74 | 0.52 | 36.23 | 7.02 | 0.25 | 0.54 | 0.61 | 0.36 |
| 95th percentile | 176.30 | 21.99 | 7.77 | 108.25 | 16.29 | 4.07 | 0.84 | 0.90 | 0.70 |
| SD | 40.96 | 4.23 | 2.53 | 24.40 | 2.99 | 1.34 | 0.10 | 0.09 | 0.11 |
| % CV | 41 | 29 | 81.28 | 36 | 27 | 81.02 | 14 | 12 | 20.20 |
| 3rd quartile | 123.18 | 17.26 | 4.22 | 82.72 | 12.92 | 2.34 | 0.77 | 0.09 | 0.61 |
| 1st quartile | 69.63 | 11.43 | 1.20 | 51.60 | 8.95 | 0.63 | 0.65 | 0.84 | 0.46 |
| 10th percentile | 55.45 | 9.76 | 0.75 | 40.08 | 7.78 | 0.42 | 0.58 | 0.72 | 0.39 |
| 90th percentile | 154.24 | 20.66 | 6.58 | 100.38 | 15.22 | 3.34 | 0.82 | 0.65 | 0.67 |

Simulation of Plasma Concentration-Time Profile Maribavir 800 mg BID in the Presence and Absence of Carbamazepine Predicted plasma concentration-time profiles of maribavir during 3 days of dosing (5 doses, starting on day 15) at 800 mg BID in the absence and presence of once daily carbamazepine QD (200 mg on day 1 and 2, and 400 mg on day 3 to day 17) were generated. For each simulation, mean concentration-time profiles for each trial with 10 subjects, with a total virtual population of 200 subjects were used. The predicted PK parameters ($C_{max}$, $AUC_{(0-12h)}$ and $C_{12h}$) for the population are shown in Table 23A. Predicted PK parameters for maribavir 800 mg BID in the presence of carbamazepine compared with PK parameters for maribavir 400 mg BID are presented in Table 24A.

Maribavir AUC and $C_{max}$ from 800 mg BID in the presence of 400 mg carbamazepine QD were marginally higher than those from maribavir 400 mg BID alone, but $C_{min}$ was similar to that of 400 mg maribavir alone, suggesting that increasing the maribavir dose from 400 mg BID to 800 mg BID can counteract the effect of carbamazepine from an efficacy perspective (mainly driven by $C_{min}$).

TABLE 23A

Predicted PK parameters for maribavir 800 mg BID in the presence and absence of carbamazepine.

| | Maribavir 800 mg BID | | | Maribavir 800 mg BID + 400 mg QD carbazepine | | | Ratio | | |
|---|---|---|---|---|---|---|---|---|---|
| | $AUC_{(0-12\,h)}$ | $C_{max}$ | $C_{12\,h}$ | $AUC_{(0-12\,h)}$ | $C_{max}$ | $C_{12\,h}$ | $AUC_{(0-12\,h)}$ | $C_{max}$ | $C_{12\,h}$ |
| | mg/L*h | mg/L | mg/L | mg/L*h PREDICTED | mg/L | mg/L | | | |
| Mean | 197.86 | 29.19 | 6.21 | 135.70 | 22.25 | 3.30 | 0.71 | 0.77 | 0.54 |
| Median | 176.68 | 27.81 | 4.68 | 126.73 | 21.61 | 2.58 | 0.71 | 0.79 | 0.56 |
| Geometric Mean | 182.50 | 28.01 | 4.37 | 127.63 | 21.48 | 2.30 | 0.70 | 0.77 | 0.53 |

TABLE 23A-continued

Predicted PK parameters for maribavir 800 mg BID in the presence and absence of carbamazepine.

|  | Maribavir 800 mg BID | | | Maribavir 800 mg BID + 400 mg QD carbazepine | | | Ratio | | |
|---|---|---|---|---|---|---|---|---|---|
|  | $AUC_{(0\text{-}12\,h)}$ | $C_{max}$ | $C_{12\,h}$ | $AUC_{(0\text{-}12\,h)}$ | $C_{max}$ | $C_{12\,h}$ | $AUC_{(0\text{-}12\,h)}$ | $C_{max}$ | $C_{12\,h}$ |
|  | mg/L*h | mg/L | mg/L | mg/L*h PREDICTED | mg/L | mg/L |  |  |  |
| 90% CI around geometric mean (lower limit) | 174.10 | 27.08 | 4.35 | 122.50 | 20.82 | 2.29 | 0.69 | 0.76 | 0.52 |
| 90% CI around geometric mean (upper limit) | 191.31 | 28.97 | 4.39 | 132.99 | 22.16 | 2.31 | 0.71 | 0.78 | 0.53 |
| $5^{th}$ percentile | 96.09 | 17.47 | 1.03 | 72.46 | 14.03 | 0.50 | 0.54 | 0.61 | 0.36 |
| $95^{th}$ percentile | 352.60 | 43.98 | 15.54 | 216.50 | 32.57 | 8.13 | 0.84 | 0.90 | 0.70 |
| SD | 81.92 | 8.47 | 5.05 | 48.79 | 5.97 | 2.67 | 0.10 | 0.09 | 0.11 |
| % CV | 41 | 29 | 81.28 | 36 | 27 | 81.02 | 14 | 12 | 20.2 |
| $3^{rd}$ quartile | 246.37 | 34.52 | 8.44 | 165.43 | 25.84 | 4.67 | 0.77 | 0.84 | 0.61 |
| $1^{st}$ quartile | 139.25 | 22.86 | 2.41 | 103.20 | 17.89 | 1.27 | 0.65 | 0.72 | 0.46 |
| $10^{th}$ percentile | 110.89 | 19.53 | 1.50 | 80.17 | 15.56 | 0.85 | 0.58 | 55.45 | 0.39 |
| $90^{th}$ percentile | 308.48 | 41.32 | 13.15 | 200.76 | 30.43 | 6.68 | 0.82 | 154.24 | 0.67 |

TABLE 24A

Predicted PK parameters for maribavir 800 mg BID in the presence of carbamazepine 400 mg QD compared with PK parameters for maribavir 400 mg BID.

|  | Maribavir 400 mg BID | | | Maribavir 800 mg BID + 400 mg QD carbazepine | | | Ratio | | |
|---|---|---|---|---|---|---|---|---|---|
|  | $AUC_{(0\text{-}12\,h)}$ | $C_{max}$ | $C_{12\,h}$ | $AUC_{(0\text{-}12\,h)}$ | $C_{max}$ | $C_{12\,h}$ | $AUC_{(0\text{-}12\,h)}$ | $C_{max}$ | $C_{12\,h}$ |
|  | mg/L*h | mg/L | mg/L | mg/L*h PREDICTED | mg/L | mg/L |  |  |  |
| Mean | 98.93 | 14.60 | 3.11 | 135.70 | 22.25 | 3.30 | 1.37 | 1.52 | 1.06 |
| Median | 88.34 | 13.91 | 2.34 | 126.73 | 21.61 | 2.58 | 1.43 | 1.55 | 1.10 |
| Geometric Mean | 91.25 | 14.01 | 2.18 | 127.63 | 21.48 | 2.30 | 1.40 | 1.53 | 1.06 |
| 90% CI around geometric mean (lower limit) | 87.05 | 13.54 | 2.16 | 122.50 | 20.82 | 2.29 | 1.41 | 1.54 | 1.06 |
| 90% CI around geometric mean (upper limit) | 95.66 | 14.49 | 2.21 | 132.99 | 22.16 | 2.31 | 1.39 | 1.53 | 1.05 |
| $5^{th}$ percentile | 48.05 | 8.74 | 0.52 | 72.46 | 14.03 | 0.50 | 1.51 | 1.61 | 0.96 |
| $95^{th}$ percentile | 176.30 | 21.99 | 7.77 | 216.50 | 32.57 | 8.13 | 1.23 | 1.48 | 1.05 |
| SD | 40.96 | 4.23 | 2.53 | 48.79 | 5.97 | 2.67 | 1.19 | 1.41 | 1.06 |
| % CV | 41 | 29 | 81.28 | 36 | 27 | 81.02 | 0.88 | 0.93 | 1.00 |
| $3^{rd}$ quartile | 123.18 | 17.26 | 4.22 | 165.43 | 25.84 | 4.67 | 1.34 | 1.50 | 1.11 |
| $1^{st}$ quartile | 69.63 | 11.43 | 1.20 | 103.20 | 17.89 | 1.27 | 1.48 | 1.57 | 1.06 |
| $10^{th}$ percentile | 55.45 | 9.76 | 0.75 | 80.17 | 15.56 | 0.85 | 1.45 | 1.59 | 1.13 |
| $90^{th}$ percentile | 154.24 | 20.66 | 6.58 | 200.76 | 30.43 | 6.68 | 1.30 | 1.47 | 1.02 |

Simulation of Plasma Concentration-Time Profiles of Maribavir 1200 mg BID in the Presence and Absence of Carbamazepine Predicted plasma concentration-time profiles of maribavir during 3 days of dosing (5 doses, starting on day 15) at 1200 mg BID in the absence and presence of once daily carbamazepine QD (200 mg on day 1 and 2, and 400 mg on day 3 to day 17) were generated. For each simulation, mean concentration-time profiles for each trial with 10 subjects, with a total virtual population of 200 subjects were used. The predicted PK parameters ($C_{max}$, $AUC_{(0\text{-}12h)}$ and $C_{12h}$ for the population are shown in Table 25A. Predicted PK parameters for maribavir 1200 mg BID in the presence of carbamazepine compared with PK parameters for maribavir 400 mg BID are presented in Table 26A.

Maribavir AUC and $C_{max}$ from 1200 mg BID in the presence of 400 mg carbamazepine QD were significantly higher (about 2-fold) than those from maribavir 400 mg BID alone. The $C_{min}$ was about 50% higher than that of 400 mg maribavir alone, suggesting that increasing the maribavir dose from 400 mg BID to 800 mg BID might be preferred to a 1200 mg BID maribavir dose to counteract the effect of carbamazepine from an efficacy perspective.

TABLE 25A

Predicted PK parameters for maribavir 1200 mg BID in the presence and absence of carbamazepine.

|  | Maribavir 1200 mg BID | | | Maribavir 1200 mg BID + 400 mg QD carbazepine | | | Ratio | | |
|---|---|---|---|---|---|---|---|---|---|
|  | $AUC_{(0-12\ h)}$ | $C_{max}$ | $C_{12\ h}$ | $AUC_{(0-12\ h)}$ | $C_{max}$ | $C_{12\ h}$ | $AUC_{(0-12\ h)}$ | $C_{max}$ | $C_{12\ h}$ |
|  | mg/L*h | mg/L | mg/L | mg/L*h PREDICTED | mg/L | mg/L | | | |
| Mean | 296.79 | 43.79 | 9.32 | 203.54 | 33.37 | 4.95 | 0.71 | 0.77 | 0.54 |
| Median | 265.02 | 41.72 | 7.02 | 190.10 | 32.41 | 3.88 | 0.71 | 0.79 | 0.56 |
| Geometric Mean | 273.75 | 42.02 | 6.55 | 191.45 | 32.22 | 3.45 | 0.70 | 0.77 | 0.53 |
| 90% CI around geometric mean (lower limit) | 261.14 | 40.62 | 6.48 | 183.75 | 31.23 | 3.42 | 0.69 | 0.76 | 0.53 |
| 90% CI around geometric mean (upper limit) | 286.97 | 43.46 | 6.62 | 199.48 | 33.24 | 3.49 | 0.71 | 0.78 | 0.53 |
| 5th percentile | 144.14 | 26.21 | 1.55 | 108.68 | 21.05 | 0.76 | 0.54 | 0.61 | 0.36 |
| 95th percentile | 528.90 | 65.97 | 23.31 | 324.74 | 48.86 | 12.20 | 0.84 | 0.90 | 0.70 |
| SD | 122.87 | 12.70 | 7.58 | 73.19 | 8.96 | 4.01 | 0.10 | 0.09 | 0.11 |
| % CV | 41 | 29 | 81.28 | 36 | 27 | 81.02 | 14 | 12 | 20.2 |
| 3rd quartile | 369.55 | 51.78 | 12.65 | 248.14 | 38.76 | 7.01 | 0.77 | 0.84 | 0.61 |
| 1st quartile | 208.88 | 34.29 | 3.61 | 154.80 | 26.84 | 1.90 | 0.65 | 0.72 | 0.46 |
| 10th percentile | 166.34 | 29.29 | 2.26 | 120.25 | 23.34 | 1.27 | 0.58 | 55.45 | 0.39 |
| 90th percentile | 462.72 | 61.98 | 19.73 | 301.14 | 45.65 | 10.02 | 0.82 | 154.24 | 0.67 |

TABLE 26A

Predicted PK parameters for maribavir 1200 mg BID in the presence of carbamazepine 400 mg QD compared with PK parameters for maribavir 400 mg BID.

|  | Maribavir 400 mg BID | | | Maribavir 1200 mg BID + 400 mg QD carbazepine | | | Ratio | | |
|---|---|---|---|---|---|---|---|---|---|
|  | $AUC_{(0-12\ h)}$ | $C_{max}$ | $C_{12\ h}$ | $AUC_{(0-12\ h)}$ | $C_{max}$ | $C_{12\ h}$ | $AUC_{(0-12\ h)}$ | $C_{max}$ | $C_{12\ h}$ |
|  | mg/L*h | mg/L | mg/L | mg/L*h PREDICTED | mg/L | mg/L | | | |
| Mean | 98.93 | 14.60 | 3.11 | 203.54 | 33.37 | 4.95 | 2.06 | 2.29 | 1.59 |
| Median | 88.34 | 13.91 | 2.34 | 190.10 | 32.41 | 3.88 | 2.15 | 2.33 | 1.66 |
| Geometric Mean | 91.25 | 14.01 | 2.18 | 191.45 | 32.22 | 3.45 | 2.10 | 2.30 | 1.58 |
| 90% CI around geometric mean (lower limit) | 87.05 | 13.54 | 2.16 | 183.75 | 31.23 | 3.42 | 2.11 | 2.31 | 1.58 |
| 90% CI around geometric mean (upper limit) | 95.66 | 14.49 | 2.21 | 199.48 | 33.24 | 3.49 | 2.09 | 2.29 | 1.58 |
| 5th percentile | 48.05 | 8.74 | 0.52 | 108.68 | 21.05 | 0.76 | 2.26 | 2.41 | 1.46 |
| 95th percentile | 176.30 | 21.99 | 7.77 | 324.74 | 48.86 | 12.20 | 1.84 | 2.22 | 1.57 |
| SD | 40.96 | 4.23 | 2.53 | 73.19 | 8.96 | 4.01 | 1.79 | 2.12 | 1.58 |
| % CV | 41 | 29 | 81.28 | 36 | 27 | 81.02 | 0.88 | 0.93 | 1.00 |
|  | 123.18 | 17.26 | 4.22 | 248.14 | 38.76 | 7.01 | 2.01 | 2.25 | 1.66 |
|  | 69.63 | 11.43 | 1.20 | 154.80 | 26.84 | 1.90 | 2.22 | 2.35 | 1.58 |
|  | 55.45 | 9.76 | 0.75 | 120.25 | 23.34 | 1.27 | 2.17 | 2.39 | 1.69 |
|  | 154.24 | 20.66 | 6.58 | 301.14 | 45.65 | 10.02 | 1.95 | 2.21 | 1.52 |

Discussion

Prospective use of the model to predict the likely outcomes of interaction with rifampicin (800 mg and 1200 mg BID maribavir), phenobarbital (400 mg, 800 mg and 1200 mg BID maribavir), phenytoin (400 mg, 800 mg and 1200 mg BID maribavir), and carbamazepine (400 mg, 800 mg and 1200 mg BID maribavir) indicated geometric mean (arithmetic mean) $C_{max}$ ratios of 0.54 (0.56), 0.72 (0.73), 0.68 (0.69), and 0.77 (0.77), respectively, for maribavir. Corresponding predicted geometric mean (arithmetic mean) $AUC_{0-12h}$ ratios were 0.35 (0.37), 0.60 (0.61), 0.57 (0.58), and 0.70 (0.71), respectively. Corresponding predicted geometric mean (arithmetic mean) $C_{12h}$ ratios were 0.04 (0.10), 0.31 (0.37), 0.30 (0.36), and 0.53 (0.54) respectively. As there was no non-linearity in the PBPK model for maribavir, the changes in exposure as a consequence of CYP3A4-mediated induction by the perpetrators were not dependent on the dose of maribavir.

Efficacy of maribavir is correlated to the trough concentrations ($C_{12h}$) of the drug. Significant reductions in $C_{12h}$ were predicted when the standard dose of 400 mg BID maribavir was combined with CYP3 A4 inducers such as rifampicin, phenobarbital, phenytoin, and carbamazepine. Simulations with higher doses of maribavir (i.e. 800 mg BID, 1200 mg BID and 1600 mg BID) were performed to determine whether the reduction in $C_{12h}$, (and hence reduction in maribavir efficacy) could be overcome by dose increase. The reduction in $C_{12h}$ due to the rifampicin induction of CYP3A4 could not be corrected by the use of up to 1600 mg BID maribavir. Use of a dose of 800 mg BID maribavir with phenobarbital resulted in a $C_{12h}$ that was 15% lower than that with 400 mg BID maribavir alone while 1200 mg BID resulted a 1.28-fold increase in $C_{12h}$. A 1200 mg BID dose of maribavir with phenytoin was also predicted to overcome the reduction in $C_{12h}$, due to CYP3A4 induction. Increasing the maribavir dose to 800 or 1200 mg BID can be used to overcome the reduction in $C_{12h}$ due to carbamazepine. Maribavir demonstrated acceptable safety/tolerability profiles with no limiting toxicity at doses up to 1200 mg BID in Phase 2 studies for the treatment of CMV infection/diseases and the predicted mean $AUC_{(0-12h)}$ and $C_{max}$ values are 292 mg/L*h and 43.4 mg/L for 1200 mg BID maribavir. The predicted $AUC_{(0-12h)}$ and $C_{max}$ values seen with maribavir dose increases, as discussed above, in the presence of inducers are below the exposure predicted for 1200 mg BID maribavir alone, therefore there is no safety concern with increasing maribavir dose from 400 mg to 800 mg, or 1200 mg in the presence of inducer. Overall, CYP3A4 inducers significantly reduce systemic exposure of maribavir; therefore maribavir dose increase is necessary when co-administration with CYP3A4 inducers is necessary. When co-administration with carbamazepine or phenobarbital is needed, maribavir dose increase to 800 or 1200 mg BID is recommended. When co-administration with phenytoin is needed, maribavir dose increase to 1200 mg BID recommendation. Rifampicin caused significant reduction in maribavir exposure which cannot be overcome by maribavir dose increase up to 1600 mg BID, therefore coadministration with rifampicin should be prohibited or alternative antibacterial therapy of lower CYP3A4 induction potential should be considered.

General note: The dose recommendations for inducers were based on arithmetic mean ratios due to the bias in the geometric mean estimates with coadministration. However, geometric mean ratios were used for dose recommendation for inhibitors.

Example 3—Co-Administration of Maribavir with Other Drugs

Drug interaction studies were summarized based on Example 2 and other available data (e.g., in vitro and clinical data). Considerations for each coadministered drug are provided in Table 1-A, and the effects of co-administration of other drugs on the pharmacokinetics of maribavir are summarized in Tables 1-B and 1-C.

TABLE 1-A

Summary of established and other potentially significant drug interactions (observed and predicted).

| Concomitant Drug Class: Drug Name | Effect on Concentration | Considerations |
|---|---|---|
| Antiarrhythmics | | |
| digoxin | ↑digoxin | Use caution when maribavir and digoxin are co-administered. Monitor serum digoxin concentrations. The dose of digoxin may need to be reduced with co-administered with maribavir |
| Anticonvulsants | | |
| Carbamazepine | ↓Maribavir | A dose adjustment of maribavir to 800 mg, twice daily when co-administered with carbamazepine |
| Phenobarbital | ↓Maribavir | A dose adjustment of maribavir to 1200 mg, twice daily when co-administered with phenobarbital |
| Phenytoin | ↓Maribavir | A dose adjustment of maribavir to 1200 mg, twice daily when co-administered with phenytoin |
| Antimycobacterials | | |
| Rifabutin | ↓Maribavir | Co-administration of maribavir and rifamutin may decrease efficacy of maribavir |
| Rifampin | ↓Maribavir | Co-administration of maribavir and rifampin may decrease efficacy of maribavir |
| Herbal Products | | |
| St. John's wort | ↓Maribavir | Co-administration of maribavir and St. John's wort may decrease efficacy of maribavir |
| Immunosuppressants | | |
| Cyclosporine | ↑Cyclosporine | Frequently monitor cyclosporine levels throughout treatment with maribavir, especially following initiation and after discontinuation of maribavir and adjust dose as needed |
| Everolimus | ↑Everolimus | Frequently monitor everolimus levels throughout treatment with maribavir, especially following initiation and after discontinuation of maribavir and adjust dose as needed |
| Sirolimus | ↑Sirolimus | Frequently monitor sirolimus levels throughout treatment with maribavir, especially following initiation and after discontinuation of maribavir and adjust dose as needed |

TABLE 1-A-continued

Summary of established and other potentially significant drug interactions (observed and predicted).

| Concomitant Drug Class: Drug Name | Effect on Concentration | Considerations |
|---|---|---|
| Tacrolimus | ↑Tacrolimus | Frequently monitor tacrolimus levels throughout treatment with maribavir, especially following initiation and after discontinuation of maribavir and adjust dose as needed |

TABLE 1-B

Summary of Changes in Pharmacokinetics of Maribavir in the Presence of Co-administered Drugs.

| Co-administered Drug and Regimen | | Maribavir Regimen | N | Geometric Mean Ratio (90% CI] of Maribavir PK with/without Co-administered Drug (No Effect = 1.00) | | |
|---|---|---|---|---|---|---|
| | | | | AUC | $C_{max}$ | $C_{tau}^{c}$ |
| Anticonvulsants | | | | | | |
| Carbamazepine[a] | 400 mg once daily | 800 mg twice daily/ 400 mg twice daily | 200 | 1.40 (1.09, 1.67) | 1.53 (1.22, 1.79) | 1.05 (0.71, 1.40) |
| Phenobarbital[a] | 100 mg once daily | 1,200 twice daily/ 400 mg twice daily | 200 | 1.80 (1.18, 2.35) | 2.17 (1.69, 2.57) | 0.94 (0.22, 1.97) |
| Phenytoin[a] | 300 mg once daily | 1,200 twice daily/ 400 mg twice daily | 200 | 1.70 (1.06, 2.46) | 2.05 (1.49, 2.63) | 0.89 (0.26, 2.04) |
| Antimycobacterials | | | | | | |
| Rifampin | 600 mg once daily | 400 mg twice daily | 14 | 0.40 (0.36, 0.44) | 0.61 (0.52, 0.72) | 0.18 (0.14, 0.25) |
| Antifungals | | | | | | |
| Ketoconazole | 400 mg single dose | 400 mg single dose | 19 | 1.53 (1.44, 1.63) | 1.10 (1.01, 1.19) | — |
| Aluminum hydroxide and magnesisum hydroxide antacid | 20 mL[b] single dose | 100 mg single dose | 15 | 0.89 (0.83, 0.96) | 0.84 (0.75, 0.94) | |

[a]Based on physiologically based pharmacokinetic modelings results from 10 trials of 20 subjects each. The maribavir dosing regimen and geometric mean ratios (5th percentile, 95 percentile) correspond to dose-adjusted maribavir with inducer vs. 400 mg twice daily without inducer.
[b]Containing 800 mg aluminum hydroxide and 800 mg magnesium hydroxide.
[c]tau is maribavir dosing interval: 12 hours.

TABLE 1-C

Changes of Pharmacokinetics for Co-administered Drug in the Presence of 400 mg Twice Daily Maribavir.

| Co-administered Drug and Regimen | | N | Geometric Mean Ratio [90% CI] of Maribavir PK with/without Co-maribavir (No Effect = 1.00) | | |
|---|---|---|---|---|---|
| | | | AUC | $C_{max}$ | $C_{trough}$ |
| Immunosuppressants | | | | | |
| Tacrolimus | stable dose, twice daily (total daily dose: 0.5-16 mg) | 20 | 1.51 (1.39, 1.65) | 1.38 (1.20, 1.57) | 1.57 (1.41, 1.74) |
| P-gp substrate | | | | | |
| digoxin | 0.5 mg single dose | 18 | 1.21 (1.10, 1.32) | 1.25 (1.13, 1.38) | — |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The invention claimed is:

1. A method of treating cytomegalovirus (CMV) infection in a patient suffering therefrom, the method comprising
   administering maribavir in an amount of 1200 mg orally twice daily, wherein the patient is a transplant recipient concomitantly exposed to or receiving an anticonvulsant selected from phenytoin or phenobarbital,
   wherein maribavir is administered prior to, concurrently with, or subsequently from the administration of the anticonvulsant.

2. The method of claim 1, wherein the anticonvulsant is phenytoin.

3. The method of claim 1, wherein the anticonvulsant is phenobarbital.

4. The method of claim 1, wherein the patient is an adult or a child of 12 years of age or older, and wherein the patient weighs at least 35 kg.

5. The method of claim 1, wherein the patient is refractory to treatment with one or more of ganciclovir, valganciclovir, cidofovir, or foscarnet.

6. The method of claim 1, wherein the patient is a hematopoietic stem cell transplant recipient.

7. The method of claim 1, wherein the patient is a solid organ transplant recipient.

* * * * *